(12) United States Patent
Troxler

(10) Patent No.: US 9,587,938 B2
(45) Date of Patent: *Mar. 7, 2017

(54) METHOD AND APPARATUS FOR DETERMINING A CHARACTERISTIC OF A CONSTRUCTION MATERIAL

(75) Inventor: Robert Ernest Troxler, Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 273 days.

This patent is subject to a terminal disclaimer.

(21) Appl. No.: 13/478,068

(22) Filed: May 22, 2012

(65) Prior Publication Data

US 2012/0227475 A1   Sep. 13, 2012

Related U.S. Application Data

(63) Continuation-in-part of application No. 12/128,556, filed on May 28, 2008, now Pat. No. 8,185,344, (Continued)

(51) Int. Cl.
*G01N 9/00* (2006.01)
*G01N 33/42* (2006.01)
(Continued)

(52) U.S. Cl.
CPC ............... *G01B 21/20* (2013.01); *G01N 9/02* (2013.01); *G01N 21/6456* (2013.01); *G01N 33/42* (2013.01); *G01N 33/383* (2013.01); *G01N 2009/024* (2013.01)

(58) Field of Classification Search
CPC G01N 9/00; G01N 9/02; G01N 33/42; G01N 33/383; G01N 21/6456;
(Continued)

(56) References Cited

U.S. PATENT DOCUMENTS

| 3,873,226 A | 3/1975 | Teach |
| 4,238,147 A | 12/1980 | Stern |

(Continued)

FOREIGN PATENT DOCUMENTS

| DE | 4135329 A1 | 4/1993 |
| DE | 4208455 A1 | 9/1993 |

(Continued)

OTHER PUBLICATIONS

Hochuli et al., Measuring the Complex Modulus of Asphalt Mixtures by Structural Wave Propagation, Mar. 19-21, 2001, 26th Annual Meeting of the Association of Asphalt Paving Technologists Aapt, Clearwater Beach, Florida, 37 pp.*

(Continued)

*Primary Examiner* — Toan Le
(74) *Attorney, Agent, or Firm* — Olive Law Group, PLLC

(57) ABSTRACT

An apparatus is provided. The apparatus is provided for interacting with a cylindrically-shaped construction material sample that defines a longitudinal axis extending from a central point of an end of the construction material sample. The apparatus includes a translation mechanism configured for rotating the construction material sample about the longitudinal axis and at least one material-interacting device spaced-apart from the translation mechanism and configured for interacting with the construction material sample.

35 Claims, 17 Drawing Sheets

Related U.S. Application Data which is a continuation of application No. 10/870,682, filed on Jun. 17, 2004, now Pat. No. 7,389,199.

(60) Provisional application No. 61/493,924, filed on Jun. 6, 2011, provisional application No. 60/478,993, filed on Jun. 17, 2003.

(51) Int. Cl.
  *G01B 21/20* (2006.01)
  *G01N 9/02* (2006.01)
  *G01N 21/64* (2006.01)
  *G01N 33/38* (2006.01)

(58) Field of Classification Search
  CPC ..... G01N 2009/024; G01N 2015/0096; G01N 2011/008; G01N 2203/0682; G01N 15/0893; G01N 5/025; G01F 17/00; G01B 11/00; G02B 21/06; G06T 7/401; G06T 7/602; C04B 7/19; C04B 18/02; C04B 28/02; C04B 2111/0075; E04C 2/06
  USPC ......... 702/156, 23, 32–33, 35, 40, 127, 150; 73/32 R, 53.07, 73, 149, 152.05, 433, 824, 73/864.91; 250/269.1, 390.05–390.06, 250/393; 324/639; 356/244; 33/555
  See application file for complete search history.

(56) References Cited

U.S. PATENT DOCUMENTS

| | | | |
|---|---|---|---|
| 4,280,354 A | 7/1981 | Wheeler et al. | |
| 4,573,131 A | 2/1986 | Corbin | |
| 4,590,367 A | 5/1986 | Ross et al. | |
| 4,705,401 A | 11/1987 | Addleman et al. | |
| 4,715,717 A | 12/1987 | Evans | |
| 4,737,032 A | 4/1988 | Addleman et al. | |
| 4,796,998 A | 1/1989 | Soma et al. | |
| 4,895,440 A | 1/1990 | Cain et al. | |
| 4,899,296 A | 2/1990 | Khattak | |
| 4,946,281 A | 8/1990 | Dell'Eva et al. | |
| 4,954,962 A | 9/1990 | Evans, Jr. et al. | |
| 4,958,306 A | 9/1990 | Powell et al. | |
| 4,978,219 A | 12/1990 | Bessho | |
| 4,979,815 A | 12/1990 | Tsikos | |
| 4,989,984 A | 2/1991 | Salinger | |
| 5,065,618 A | 11/1991 | Hodges, Sr. et al. | |
| 5,085,502 A | 2/1992 | Womack et al. | |
| 5,155,558 A | 10/1992 | Tannenbaum et al. | |
| 5,362,176 A | 11/1994 | Sovik | |
| 5,371,588 A | 12/1994 | Davis et al. | |
| 5,396,510 A | 3/1995 | Wilson | |
| 5,412,420 A | 5/1995 | Ellis | |
| 5,471,303 A | 11/1995 | Ai et al. | |
| 5,484,227 A | 1/1996 | Ikeda et al. | |
| 5,531,520 A | 7/1996 | Grimson et al. | |
| 5,546,123 A | 8/1996 | Ikeda et al. | |
| 5,570,183 A | 10/1996 | Wiles | |
| 5,774,374 A | 6/1998 | Scott et al. | |
| 5,790,243 A | 8/1998 | Herr | |
| 5,835,053 A | 11/1998 | Davis | |
| 5,952,561 A | 9/1999 | Jaselskis et al. | |
| 6,005,959 A | 12/1999 | Mohan et al. | |
| 6,028,672 A | 2/2000 | Geng | |
| 6,028,948 A | 2/2000 | Kil et al. | |
| 6,049,384 A | 4/2000 | Rudd et al. | |
| 6,061,126 A | 5/2000 | Yoshimura et al. | |
| 6,068,060 A | 5/2000 | Ohtomo et al. | |
| 6,100,537 A | 8/2000 | Abraham et al. | |
| 6,113,309 A | 9/2000 | Hollon et al. | |
| 6,215,317 B1 | 4/2001 | Siddiqui et al. | |
| 6,230,552 B1 | 5/2001 | Abe et al. | |
| 6,269,197 B1 | 7/2001 | Wallack | |
| 6,310,964 B1 | 10/2001 | Mohan et al. | |
| 6,321,589 B1 | 11/2001 | Regimand | |
| 6,328,634 B1 | 12/2001 | Shen et al. | |
| 6,407,818 B1 | 6/2002 | Whitehouse | |
| 6,434,257 B1 | 8/2002 | Mohan et al. | |
| 6,492,641 B1 | 12/2002 | Dep et al. | |
| 6,512,239 B1 | 1/2003 | Weiss et al. | |
| 6,679,106 B1 | 1/2004 | Sawa et al. | |
| 7,197,425 B2 | 3/2007 | Masuyama et al. | |
| 7,389,199 B2 * | 6/2008 | Troxler et al. | 702/156 |
| 8,185,344 B2 | 5/2012 | Troxler et al. | |
| 2002/0180865 A1 | 12/2002 | Lee et al. | |
| 2004/0017563 A1 | 1/2004 | James et al. | |
| 2004/0090634 A1 | 5/2004 | Mathur et al. | |
| 2005/0021285 A1 | 1/2005 | Troxler et al. | |
| 2007/0084273 A1 | 4/2007 | Hare et al. | |

FOREIGN PATENT DOCUMENTS

| | | |
|---|---|---|
| EP | 0595438 A2 | 5/1994 |
| EP | 1046478 A1 | 10/2000 |
| EP | 1225421 A2 | 7/2002 |
| EP | 1636543 | 3/2006 |
| GB | 2218513 A | 11/1989 |
| SU | 930069 A1 | 5/1982 |
| SU | 1318812 A1 | 6/1987 |

OTHER PUBLICATIONS

Yongping Wang, Quantification of the Spatial Gradient of Local Volume Fraction from Tomography Images, May 2002, M.S. Degree Thesis, the Department of Civil and Environmental Engineering, Louisiana State University and Agricultural and Mechanical College, 94 pp.*
International Search Report and Written Opinion for related PCT application No. PCT/US12/041163; (ISA/RU)all references cited herein.
Examination Report for EP patent application 04 755 511.5-2113 dated Nov. 17, 2010.
"Combatting Pavement Roughness with Rosan," Focus, Oct. 2001.
Johannesson and Thomgren, "Advances in CMOs Technology Enable Higher Speed True 3D-Measurements," Dr. Mattias Johannesson and Hakan Thorngren, Integrated Vision Products Inc. 2000.
Office Action from the Patent Office of the People's Republic of China for Chinese Patent Application No. 200480023497.3 dated Aug. 17, 2007.
Notice of Allowance for U.S. Appl. No. 10/870,682 dated Feb. 14, 2008.
Office Action for U.S. Appl. No. 10/870,682 dated Aug. 31, 2007.
Office Action for U.S. Appl. No. 10/870,682 dated Jan. 31, 2007.
Restriction/Election Requirement for U.S. Appl. No. 10/870,682 dated Aug. 2, 2006.
"Standard Test Method for Measuring Pavement Macrotexture Depth Using a Volumetric Technique," American Society for Testing and Materials (ASTM), ASTM Designation: E 965-96, 2000.
"Standard Practice for Calculating Pavement Macrotexture Mean Profile Depth," American Society for Testing and Materials (ASTM), ASTM Designation: E 1845-96 (Reapproved 2005).
Related U.S. Appl. No. 13/490,398, filed Jun. 6, 2012, not yet published.
"Standard Terminology Relating to Vehicle-Payment Systems," American Society for Testing and Materials (ASTM), ASTM Designation: E 867-06, 2000.
Saarenketo and Scullion, "Road Evaluation with Ground Penetrating Radar," Journal of Applied Geophysics 43 (2000) 119-138, Elsevier Jun. 10, 1999.
Search Report for European Patent Application No. 04 755 511.5, a related European patent application, dated Jul. 22, 2015.
Canadian Examination Search Report, Application No. 2,836,797, dated Sep. 23, 2016.

* cited by examiner

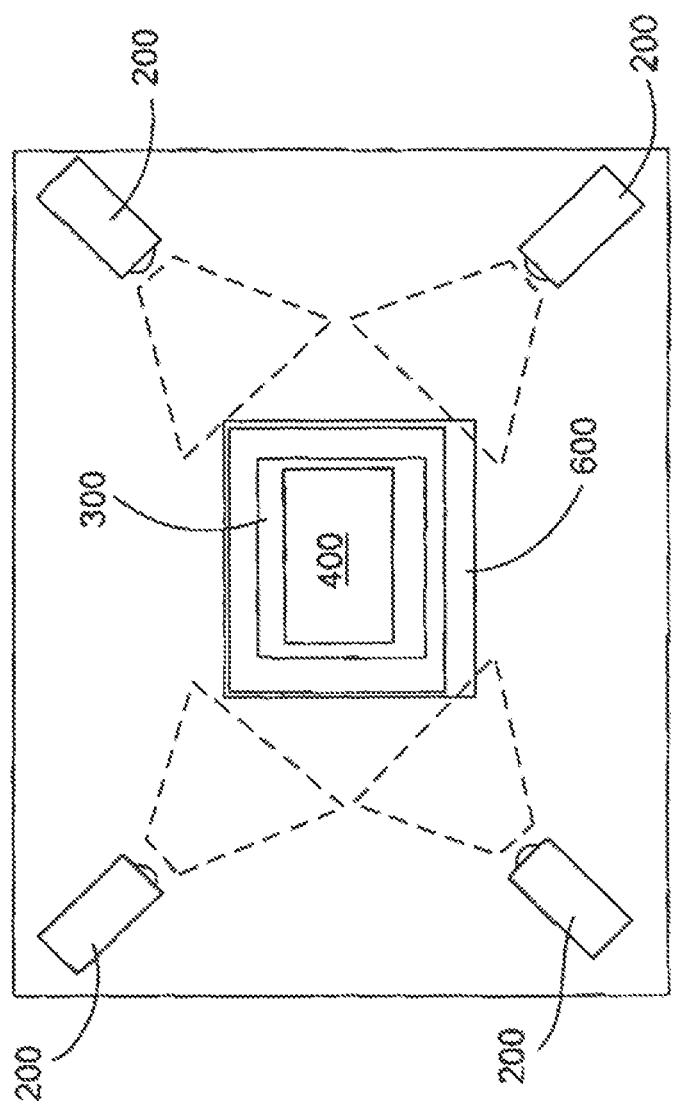

METHOD AND APPARATUS FOR DETERMINING A CHARACTERISTIC OF A CONSTRUCTION MATERIAL

CROSS-REFERENCE TO RELATED APPLICATIONS

This application claims priority to U.S. Provisional Patent Application No. 61/493,924 filed on Jun. 6, 2011 and U.S. patent application Ser. No. 12/128,556 filed on May 28, 2008, now U.S. Pat. No. 8,185,344 which claims benefit of U.S. patent application Ser. No. 10/870,682 filed on Jun. 17, 2004, now U.S. Pat. No. 7,389,199, which claims the benefit of U.S. Provisional Application No. 60/478,994 filed Jun. 17, 2003, the entire contents of which are hereby incorporated by reference.

TECHNICAL FIELD

The subject matter described herein relates to an apparatus and method for determining at least one dimension of a construction material. Particularly, the subject matter described herein relates to an apparatus and method for determining at least one dimension of a construction material sample.

BACKGROUND

The construction industry relies on materials testing for design, quality control and quality assurance of various construction projects. Material density and specific gravity are among some of the critical parameters of materials testing. The pavement construction industry, in particular, uses material density and specific gravity in the design and quality determinations of natural and manufactured paving materials.

In the asphalt paving industry, air void contents of soils, hot-mix asphalt laboratory prepared specimens or cored pavement specimens are used, for example, to determine the quality of the mix design, the plant-produced hot-mix, sub-base preparation and in general, the pavement construction. The air void content of compacted specimens is determined, in some instances, as a ratio of the actual specific gravity of the compacted specimen (bulk specific gravity) to the theoretical maximum specific gravity of the loose asphalt mixture.

The determination of the maximum specific gravity or density of the loose asphalt mixtures may have some limitations that affect the accuracy of the air void content measurement. Furthermore, methods of determining bulk specific gravity are highly operator dependent and therefore may yield highly variable results, also affecting the air void content determination. Currently, there are three generally accepted practices or methods of determining the bulk specific gravities of compacted asphalt specimens. These methods are (1) gamma attenuation; (2) applications of Archimedes' principle; and (3) dimensional analysis.

Gamma attenuation technology can be used to provide bulk density of a compacted asphalt specimen by measuring its electron density as described, for example, in U.S. Pat. No. 6,492,641 to Dep et al. The electron density is determined by the intensity and energy distribution of gamma radiation traversing the sample. The gamma radiation is typically emitted from low-level radiation cesium sources and detected by a sensitive sodium iodide detector. The resulting measurement of the electron density must then be normalized by the height (or thickness) of the specimen. However, while the electron density determination is generally precise and reliable, the gamma attenuation method may be limited by the ability of the operator to measure the height of the specimen with accuracy and precision.

ASTM D3549 is a standard test method for thickness or height determination of compacted bituminous paving mixture specimens. The standard specifies that an average of four measurements, spaced apart at 90 degree intervals, should be used to approximate the height of the specimen. It further suggests that ends of the specimen that are not horizontal relative to the vertical axis of the cylinder shall be sawn flat and horizontal. However, there are several problems associated with this method. For example, in some cases, the operator may not ensure that the ends of the specimen are flat and horizontal, thereby introducing error into the height measurement because the end-to-end (or peak-to-peak) caliper measurements will not be reliable height measurements of the specimen. In such instances, the root-mean-square height may be a more accurate measure of the specimen height for density determinations. Another source of error in such a height measurement is that four measurements with the calipers may not provide enough data points to property represent the true sample height, especially if the specimen is not a true right cylinder and/or if the ends thereof are irregular or sloped. Even if the operator uses extreme care and diligence in measuring the specimen height with the calipers, the calipers are not necessarily capable of properly measuring the irregular or uneven surfaces. Optical methods can also be used to automatically obtain height measurements, and conversely, ultrasonic or sound waves operated in a reflection mode could obtain average distances to the surface of a cylinder with respect to a reference position or plane.

One widely used method of determining the bulk specific gravity of an asphalt mix specimen is by determining the mass to volume ratio of the specimen. Mass determinations are generally highly reliable through the use of state of the art balances and scales that are readily available in the marketplace. The volume measurement, however, is typically far less reliable than the mass determination. Several different methods of volume measurement incorporate the Archimedes' principal of water displacement. Another method of obtaining a volume measurement utilizes a dimensional analysis approach with calipers or micrometers.

The Archimedes' principal approximates the volume of a solid by determining the volume of water displaced by the solid when the solid is submerged in an adequately sized water bath. Generally, the ratio of the mass of water displaced to the specific gravity of the water is the resulting volume of the solid. However, in some instances, the determined volume may be adversely affected by water seeping into interconnected voids within the solid. In addition, the density of water is not constant and may be affected by temperature, impurities, or even an inconsistent water source. Consequently, the true volume of the solid may be an illusory quantity affecting the accuracy of the determined specific gravity and density of the solid, as well as the amount of water that is able to seep into the solid. However, another issue with the water displacement method is that submerging the sample in water is a destructive process. Though the sample may be dried after immersion, even very careful drying procedures do not typically provide repeatable specific gravity determination results for that sample in subsequent tests. The damage thus done to the specimen generally prohibits the use thereof in other material testing procedures. In many instances, the water becomes contained and trapped in the core volume and renders the core unusable for future quality testing.

Several AASHTO or ASTM standards utilize this water displacement principal in the determination of bulk specific gravity of compacted asphalt mixtures. However, basically all of these methodologies include inherent sources of error, typically depending on the conditions under which the procedures are performed. The saturated surface dry (SSD) method (AASHTO T166/ASTM D2726) tends to underestimate the volume of the specimen, thereby overestimating its bulk specific gravity or density. In order to overcome the limitations associated with the SSD method, techniques have been introduced that require coating the specimen with paraffin or parafilm (AASHTO T275/ASTM D1188), or vacuum sealing the specimen inside a plastic or poly-material bag(s) (ASTM D6752) as described, for example, in U.S. Pat. No. 6,321,589 to Regimand. However, these methods may overestimate the specimen volume by bridging the surface voids of the specimen, thus providing a resulting bulk specific gravity that is often lower than the true value of bulk specific gravity for that specimen. In addition, such methods may also require correction for the mass and volume of the coating or vacuum sealing bag, which may also introduce errors into the calculations.

The dimensional analysis method for determining the bulk specific gravity of the specimen approximates the volume by physically measuring the height and diameter dimensions of the specimen with calipers or micrometers. The specific gravity determined by the dimensional analysis method, however, is typically lower than the specific gravity determined by the water displacement method since dimensional analysis using calipers or a micrometer does not consider surface voids or other irregular surface features of the specimen. The asphalt or concrete later is established on top of a soil base or sub base aggregate mixture. The base of the road bed also has density and moisture demands necessary for a successful top layer.

Another characteristic that may be important in the construction and road paving industry is the in-place density of a compacted soil or sub-base material. These "field density" measurements are sometimes found using nuclear testing equipment as described in ASTM 2992. Alternatively before high quality instruments were used for measuring field density, it was useful to determine the volume of the void or a "hole" defined in a construction material after removal of the soil for testing. By weighing the removed soil and calculating the volume of the void, the density of the soil in the field could then be calculated as measured.

In the past, sand cone and rubber balloon methods have been employed to measure the in-place density of compacted material. The sand cone method (ASTM D1556) involves pouring a dry sand of a known density or specific gravity into an excavated hole. The weight of the sand poured into the hole is then obtained and the volume could then be calculated since the density of the sand was known. The sand cone method is disadvantageous though because the test takes time to complete and the test cannot be performed in soils where water seepage occurs in the hole. Furthermore, the packing density of the sand as it is poured into the excavated hole can be variable due to vibrations, moisture content, and other variables, including potentially hundreds of pounds of sand that must be calibrated in the lab and hauled around to the testing sites.

The rubber balloon method (ASTM D2167) involves placing a water device including a balloon on the opening of the hole and then filling the balloon with water, at a predetermined pressure, until the hole is filled with the water balloon, while simultaneously watching and recording the graticule on the water column. The volume of water in the balloon is determined and equals the volume of the hole. This test is undesirable because the rubber balloon method may deform the excavated hole because of the pressure placed on the balloon, thus causing inaccuracies in the measured volume. Additionally, the balloon may not fill an irregularly shaped hole, and may not be appropriate as rougher soil surfaces typically puncture the balloon, causing the technician to do a field repair and find a new location to excavate.

In light of these limitations in being able to reliably determine the specimen height or other dimensions using existing technologies, there exists a need for a more reliable method for providing accurate dimensional values for a specimen. A method and/or apparatus is also needed that reduces the effect of operator judgment in determining specimen height or other dimensions so that single-laboratory and/or multi-laboratory variations do not affect the evaluations of the asphalt mix specimens. In addition, such an apparatus and/or method should be capable of nondestructively evaluating the specimen. A method and/or apparatus is also needed to easily, accurately, and time efficiently determine the volume of an excavated hole.

SUMMARY

The above and other needs are met by the subject matter disclosed herein which, in one embodiment, provides an apparatus for interacting with a cylindrically-shaped construction material sample. The sample is of the type defining a longitudinal axis that extends from a central point of an end of the construction material sample. The apparatus includes a translation mechanism configured for rotating the construction material sample about the longitudinal axis and at least one material-interacting device spaced-apart from the translation mechanism and configured for interacting with the construction material sample.

According to one or more embodiments, the translation mechanism is at least one roller wheel positioned about the construction material sample and configured for rotating the construction material sample.

According to one or more embodiments, the at least one roller wheel is operably coupled to a motor for providing rotational forces thereto.

According to one or more embodiments, the apparatus includes a housing that carries the translation mechanism and the construction material sample.

According to one or more embodiments, the housing is translatable from a first position to at least a second position.

According to one or more embodiments, the at least one material-interacting device includes a plurality of material-interacting devices spaced-apart from the translation mechanism.

According to one or more embodiments, the material-interacting device is configured for determining at least one measurement of the construction material sample.

According to one or more embodiments, the material-interacting device is configured to manipulate the at least one measurement to determine a characteristic of the construction material sample.

According to one or more embodiments, the characteristic is one of density, volume, and moisture content.

According to one or more embodiments, the apparatus includes one of a light point, a light line, or a wave front directed on a surface of the construction material sample for interacting therewith.

According to one or more embodiments, the apparatus is configured for using one of sound, ultrasound, light, and radiation directed on the construction material sample for interacting therewith.

According to one or more embodiments, a method is provided. The method includes rotating a cylindrically-shaped construction sample material along a longitudinal axis of the material and interacting, using a material-interacting device, with the construction sample material to determine at least one measurement thereof.

According to one or more embodiments, rotating the cylindrically-shaped construction sample material comprises using at least one roller wheel positioned about the construction sample material for rotating the construction sample material.

According to one or more embodiments, the method includes manipulating a plurality of the at least one measurements of the construction material sample for determining a characteristic thereof.

According to one or more embodiments, the method includes projecting one of a light point, a light line, or a wave front on a surface of the construction material sample for interacting therewith.

According to one or more embodiments, the method includes using one of sound, ultrasound, light, and radiation for interacting with the construction material sample.

According to one or more embodiments, the at least one material-interacting device further includes at least one sample-imaging device and the characteristic further comprises at least a partial image of the void.

According to one or more embodiments, the characteristic is one of height, shape, texture, color, aggregate size, or combinations thereof.

According to one or more embodiments, the method includes manipulating the characteristics to create a histogram of the characteristics.

The proposed methods and apparatuses thus eliminate the need for a destructive or otherwise sample-impairing testing method such as, for example, the Archimedes' water displacement methods. Whether an accurate height determination for the gamma ray attenuation method or an accurate volume determination for the dimensional analysis method is desired, the technology disclosed herein minimizes or eliminates the operator judgment and/or bias limitations previously discussed with respect to existing methods.

In some instances, the test method and apparatus for determining specimen height, shape, color and/or volume can be applied to other general construction and/or paving-related materials such as loose soils and aggregates, portland cement, asphalt and concrete cylinders, and many other applications.

The improvement in volume, shape, and/or height measurement accuracy and/or definition will, in turn, provide for more reliable density and specific gravity determinations. Thus, a subsequent effect will be improved design, quality control, and quality assurance of construction and/or paving related materials. Further benefits may include, for example, ultimately improved structures and a reduction in disputes between owner and contractor that result from the uncertainty of test results. Thus, embodiments of the subject matter disclosed herein provide significant advantages as disclosed, described, and further detailed herein.

BRIEF DESCRIPTION OF THE DRAWINGS

The subject matter described herein will now be explained with reference to the accompanying drawings of which:

FIG. 2A is a schematic of an apparatus for determining at least one surface characteristic of a construction material sample, implementing a plurality of sample-interacting devices, according to one embodiment of the subject matter disclosed herein;

DETAILED DESCRIPTION

The present subject matter will be described more fully hereinafter with reference to the accompanying drawings, in which some, but not all embodiments of the subject matter disclosed herein are shown. Indeed, the subject matter disclosed herein may be embodied in many different forms and should not be construed as limited to the embodiments set forth herein; rather, these embodiments are provided so that this disclosure will satisfy applicable legal requirements. Like numbers refer to like elements throughout.

Figure 1A:
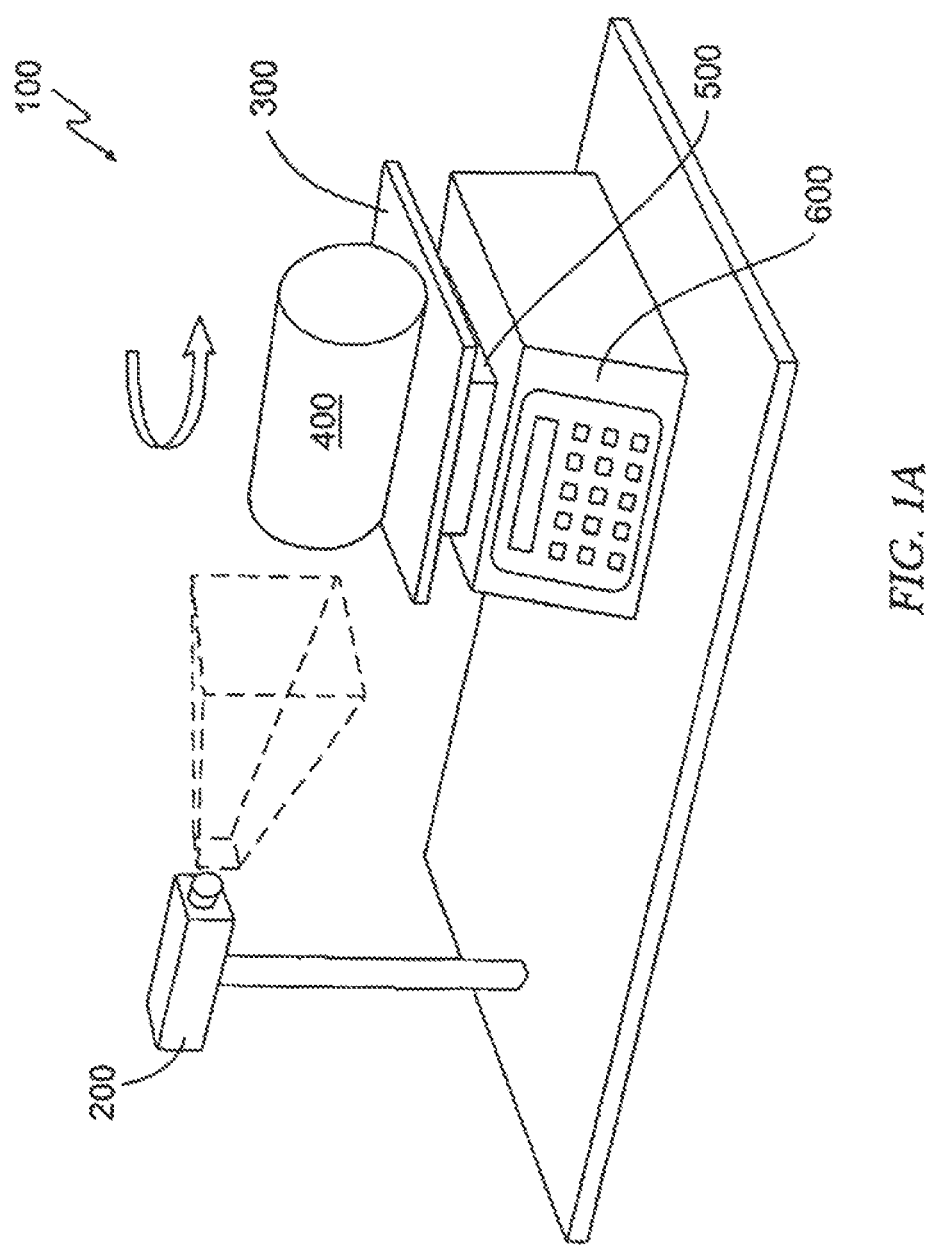
FIGS. 1A and 1B are schematics of an apparatus for determining at least one surface characteristic of a construction material sample, implementing a single sample-interacting device, according to one embodiment of the subject matter disclosed herein.
Figure 1B:
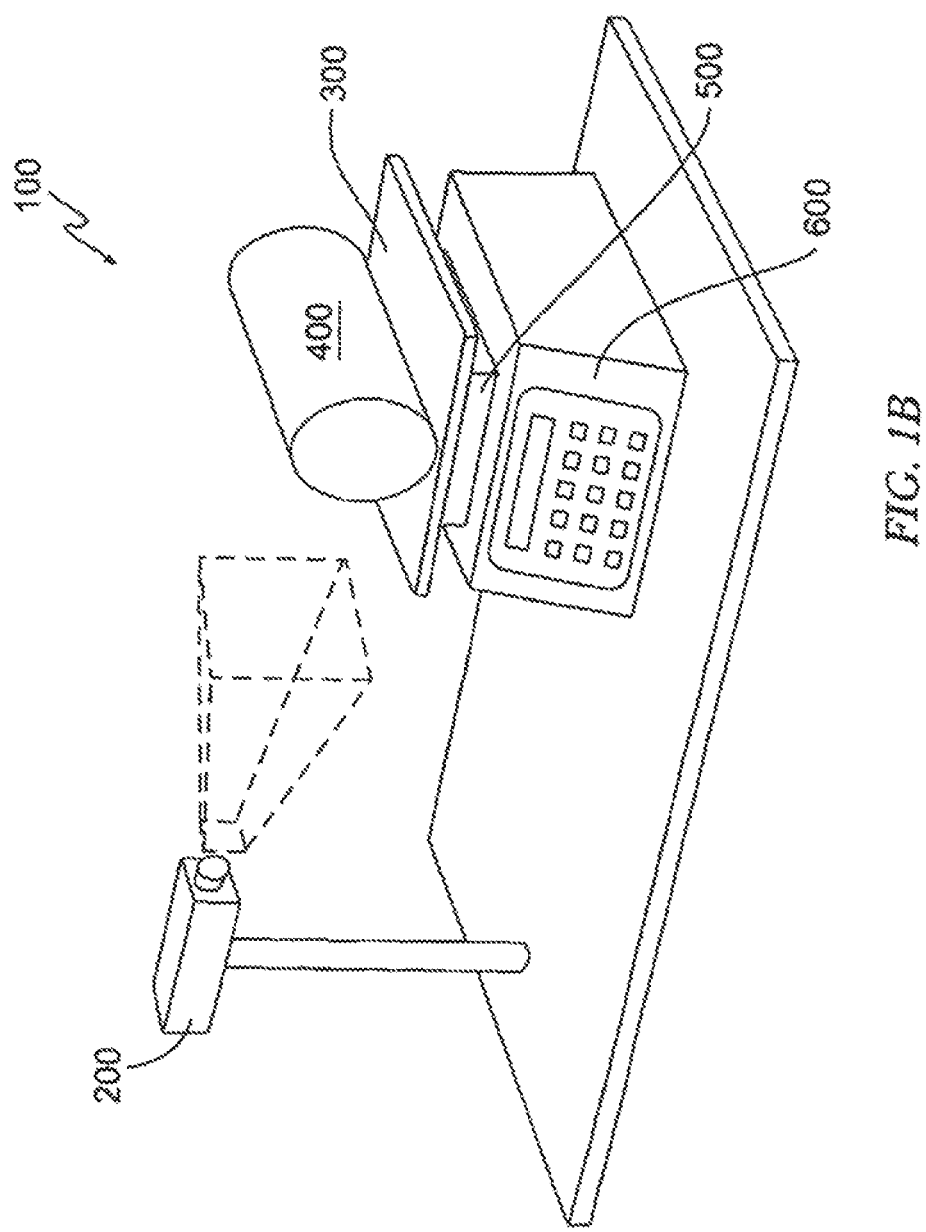

FIGS. 1A and 1B illustrate an apparatus adapted to determine at least one surface characteristic of a construction and/or paving-related material sample according to one embodiment of the subject matter disclosed herein, the apparatus being indicated generally by the numeral 100. Apparatus 100 includes at least one sample-interacting device 200 and a sample holder 300 configured to be capable of supporting a sample 400 of a paving-related material or other construction material. Note that the term "paving-related material" as used herein refers to, for example, uncompacted bituminous paving mixtures, soil bases and sub-bases, loose soils and aggregates, as well as field cores and laboratory prepared specimens of compacted bituminous paving material, while the term "construction material" as used herein is more general and includes, for example, paving-related materials, Portland cement, concrete cylinders, and the like. In situ field measurements refer to obtaining the characteristic of a pavement or soil material in the field using destructive or non-destructive methods.

Sample-interacting device 200 may use, for example, a point source, a line source, or a wave source to provide, for instance, light, sound, ultrasound, radiation, physical contact, and/or other medium for allowing at least one surface characteristic of sample 400 to be determined. One skilled in the art will appreciate that such a device 200 may be appropriately configured to use the light, sound, ultrasound, radiation (including, for example, microwave radiation or infrared radiation), physical contact and/or other medium to perform, for example, a measurement of at least one surface characteristic, such as a dimension, of sample 400 using, for instance, a reflectance methodology, a transmission methodology, a duration methodology, a contact methodology, or any other suitable methodology, wherein device 200 may include, for example, at least one corresponding and appropriate emitter/detector pair, or appropriate sensors, for measuring the at least one surface characteristic. For instance, device 200 may be configured to use structured light, laser range finders, or x-rays for non-contact-type measurements; linear variable differential transformers (LVDT) or other physical mechanisms for contact-type measurements; or any other suitable measuring technology such as range cameras, range imaging, confocal scanning, conoscopic holography or imaging, focal plane imaging, raster scans with lines or points. For example, an optical methodology or a photographic methodology such as, for instance, stereo-vision techniques, may be used for performing 3D profiling. Various imaging devices such as scanners or cameras may also be suitable in this regard where the appropriate determination of a surface characteristic(s), such as a dimension, may be accomplished by associated software or image processing procedure executed on a computer device 600 associated with sample-interacting device(s) 200. In some instances, device 200 may comprise, for example, a single or multi-dimensional profiler device such as that made by, for instance, Shape Grabber, Inc. of Ottawa, Ontario, Canada or National Optics Institute of Sainte-Foy, Quebec, Canada, or INO of Canada. However, one skilled in the art will appreciate that many other sample-interacting devices may be implemented within the spirit and scope of the subject matter disclosed herein.

Sample holder 300 is configured to hold sample 400 with respect to sample-interacting device 200 so as to allow sample-interacting device 200 to determine the appropriate surface characteristic(s) of sample 400. Such a surface characteristic may include, for example, a dimension, a texture, a roughness, or other identifiable surface aspect of sample 400, including identification and/or quantification of voids, irregularities, or other features of the sample surface. In certain situations, sample-interacting device 200 may be configured such that the necessary or desired surface characteristic(s) of sample 400 can be determined with sample 400 held in one position by sample holder 300. However, in instances, where sample 400 has a complex three-dimensional configuration, an appropriate determination or measurement may not be possible with sample 400 in a single position with respect to sample-interacting device 200. Accordingly, in instances where a second determination or measurement is necessary or desirable to produce an accurate representation of, for example, the dimensional measurement(s) of sample 400, sample 400 may be moved from a first position to a second position with respect to sample holder 300 for the second measurement. However, significant inaccuracies may be introduced if sample 400 is moved unless a common reference point with respect to sample 400 by which the two measurements must be coordinated is attained. Further, in other instances, sample 400 may be irregularly shaped or, in the case of aggregates, soils, sands, or the like, configured such that it may be inconvenient or otherwise not practically possible to hold sample 400 with respect to sample-interacting device 200, or move sample 400 to another position, to allow the appropriate dimension(s) of sample 400 to be measured.

Accordingly, one advantageous aspect of the subject matter disclosed herein in this regard is the implementation of a computer analysis device 600 capable of executing a software package for analyzing the surface characteristic(s) of sample 400 determined by at least one sample-interacting device 200 in order to extract desired information, while overcoming some of the inaccuracies encountered in obtaining a three-dimensional representation of a sample. For example, engineering/modeling/reverse engineering software such as, for instance, ProEngineer, Matlab, Geomagic Studio, or other appropriate package being executed by computer device 600, can be configured to receive the at least one surface characteristic determined by sample-interacting device 200. For instance, sample-interacting device 200 using a point source of light may be configured to detect the behavior of the light interacting with sample 400, wherein the detected light may be indicative of coordinates or distances of each of the measured points on sample 400 with respect to sample-interacting device 200. Accordingly, an increased number of measurements of sample 400 with such a point source, and the proximity of subsequent measurements to previous measurements may directly affect the resolution of the representation of sample 400 obtained from that process. That is, a dense "point cloud" may provide a significantly higher resolution of the surface characteristic(s) of sample 400 as compared to very few point measurements distributed across the surface of sample 400. However, the resolution necessary to obtain appropriate and valid results of the at least one surface characteristic of sample 400 is not limited hereby in any manner and one skilled in art will appreciate that such resolution is a matter of choice associated with the desired result to be achieved. Sample-interacting device 200 may be configured to interact with one surface, multiple surfaces, or all surfaces of a sample.

Figure 2B:
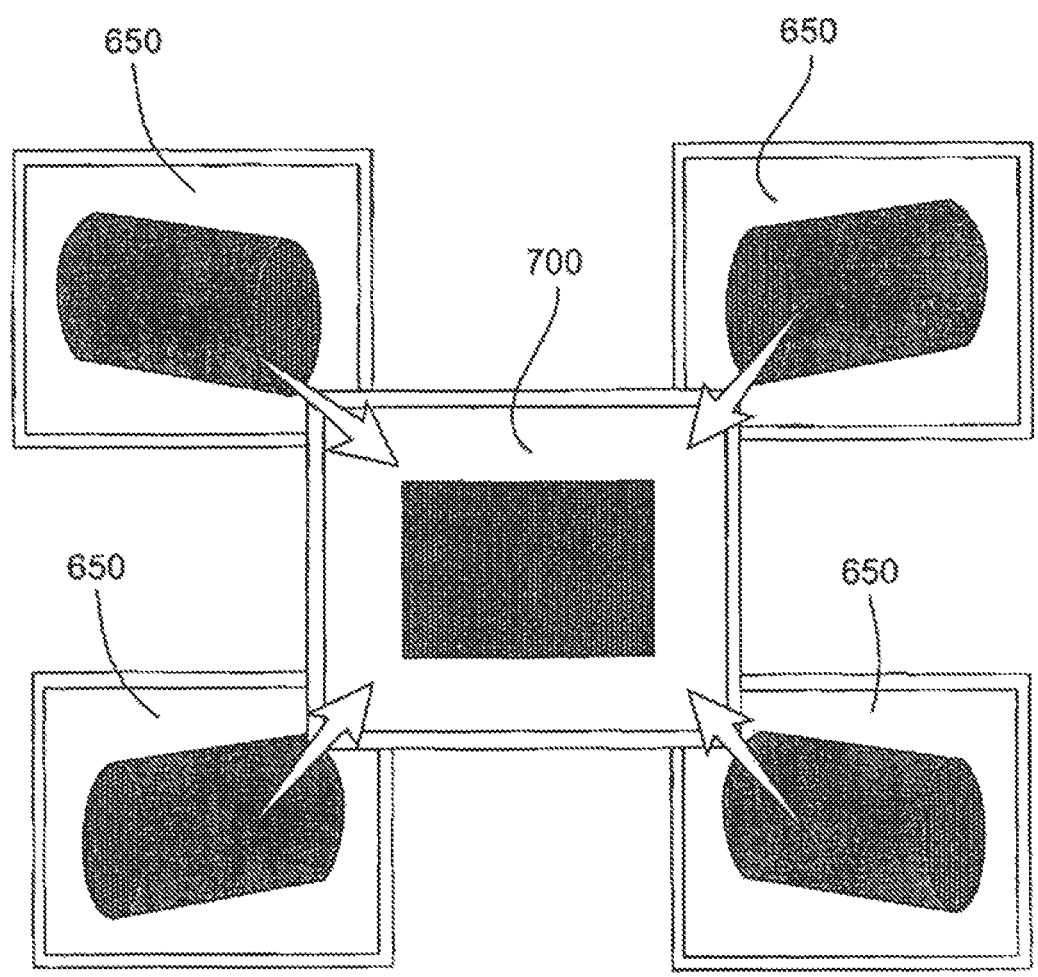
FIG. 2B is a schematic of a plurality of surface characteristics, in the form of images of the construction material sample, determined by the plurality of sample-interacting devices shown in FIG. 2A, and a multi-dimensional representation of the construction material sample formed by combining the images, from which a volume of the construction material sample can be obtained, according to one embodiment of the subject matter disclosed herein.

FIGS. 1A and 1B further illustrate sample 400 being moved with respect to sample-interacting device 200 about a vertical axis defined by sample holder 300, wherein such movement may be accomplished manually (by the operator physically rotating the sample 400 on the sample holder 300) or in an automated manner such as by a motorized or mechanized system associated with and for rotating sample holder 300 so as to rotate sample 400. The rotation for example could be accomplished by resting a cylindrical sample on a rolling mechanism, while spinning and rotating the sample with respect to the surface measuring device. In other instances, sample 400 may be stationary and sample-interacting device 200 moved around sample 400. In still other instances, as shown in FIG. 2A, a plurality of sample-interacting devices 200 may be implemented such that moving either sample 400 or sample-interacting device(s) 200 may not be necessary in order to determine or capture the desired surface characteristic(s) of sample 400. One skilled in the art will also appreciate that, in some instances, that a sample holder 300 may not be a positive aspect of apparatus 100. That is, in some instances, sample 400 may be, for example, supported by at least one sample-interacting device 200, whereby at least one sample-interacting device 200 is configured to determine the desired surface characteristic(s) of sample 400 while providing support therefor. In other instances, sample-interacting device(s) 200 may be configured to act upon a sample 400 in situ and, as such, does not require a sample holder 300 for supporting sample 400. More particularly, for example, ASTM E 965 is a standard for determining the surface texture of a roadway and involves spreading a calibrated sand on the roadway and then spreading that sand out across the roadway until a dispersed condition is met. The diameter of the sand patch is then measured, whereby the area of the sand patch and the known density of the calibrated sand may be used to determine the surface roughness of the roadway. This is typically the same type of sand used in ASTM D 1556. According to embodiments of the subject matter disclosed herein may be used to determine surface roughness by implementing a sample-interacting device 200 configured to be moved relative to the roadway so as to interact with sample 400 in situ, thereby obviating the need for a sample holder 300 per se. The surface characteristic(s) determined by sample-interacting device 200 would then be transferred to computer device 600 to determine the nature of the surface characteristic(s) and if desirable, at least one dimension of sample 400 (in this instance, the distance between sample-interacting device 200 and sample 400 can be indicative of the texture of the surface of sample 400 and thus an average separation distance can be determined, wherein the average separation distance may be related over an area to, for example, the volume of a void or an area characteristic of the roadway in that vicinity). As illustrated in FIG. 2B, multiple images may be stitched together to form one complete image of sample 400.

In one or more alternate embodiments of the subject matter disclosed herein, as shown in FIGS. 3A, 3B, 15, and 16, sample holder 300 may be configured with a first portion 320 and a second portion 340, wherein first and second portions 320, 340 are configured to cooperate to hold or merely support sample 400 such that appropriate dimension or other measurement(s) can be determined by a dimension-measuring device (as one form of a sample-interacting device 200). That is, in one embodiment, first portion 320 may be disposed at a selected position with respect to sample-interacting device 200. Second portion 340 may then optionally engage sample 400 before second portion 340 is interfaced with first portion 320 in an appropriate manner. For example, first portion 320 may define a keyway (not shown) configured to receive a key (not shown) protruding from second portion 340 such that, when interfaced, the first and second portions 320, 340 will hold sample 400 in a known position with respect to sample-interacting device 200. In any instance, first and second portions 320, 340 are configured so as to define a coordinate system with respect to sample-interacting device 200. That is, when second portion 340 is interfaced with first portion 320, sample 400 is located within a coordinate system recognized by sample-interacting device 200. In other instances, first and second portions 320,340 may be used by an appropriate software analysis package being executed by a computer device 600, as previously described, to define a coordinate system for analyzing sample 400. First and second portions may rotate on several axes with respect to the interacting device 200.

Figure 4:
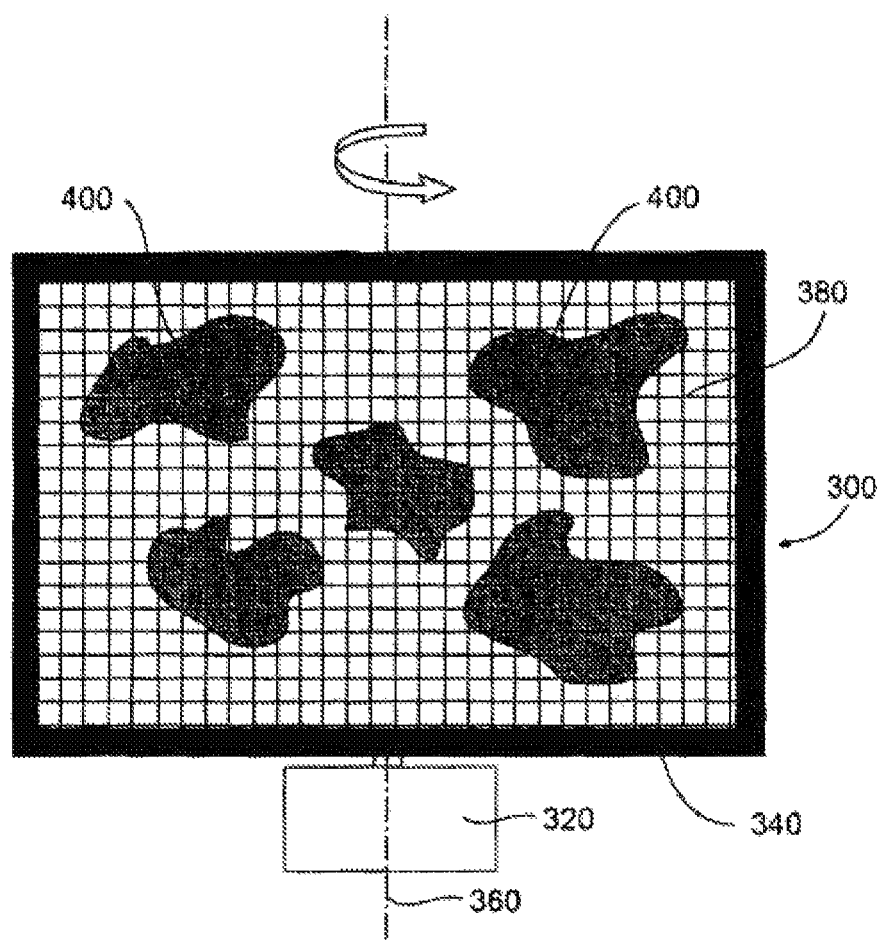
FIG. 4A is a schematic of an alternate sample holder for an apparatus for determining at least one dimension of a construction material sample, according to one embodiment of the subject matter disclosed herein, while in one or more embodiments, a flat surface that holds the aggregates, a single grid that the aggregates sit on, or multiple grids where the samples are held between two could be employed.
FIG. 4B is a schematic of an alternate sample holder for an apparatus for determining at least one dimension of a construction material sample holder similar to the sample holder depicted in FIG. 4A in which the sample holder is translating relative to an imaging device according to one embodiment of the subject matter disclosed herein. A directional arrow is provided to signify moving of the sample holder, or, alternatively, movement of a conveyor line on which the construction material is resting.

In one example, if sample 400 comprises a generally cylindrical compacted field core, the second portion 340 of sample holder 300 may be configured as any appropriately shaped or designed element about the circumference of sample 400. Accordingly, first portion 320 of sample holder 300 may be configured to receive second portion 340 such that the axis of sample 400 is generally horizontal. In such a configuration, second portion 340 may be rotated with respect to first portion 320 between measurements by sample-interacting device 200 such that the sample 400 is caused to rotate about its axis. In other instances, for example, where sample 400 comprises an aggregate, sample holder 300 may be configured as, for instance, one or more screens or trays 380 for supporting the aggregate (for example, two opposing screens 380 having the aggregate retained therebetween, or one surface can support the aggregate for imaging) with respect to sample-interacting device 200 so as to allow the appropriate dimensions or other surface characteristics of the components of the aggregate to be measured as shown, for example, in FIG. 4. As such, one skilled in the art will appreciate that embodiments of the subject matter disclosed herein may be useful to determine the dimensions or other surface characteristics of many different configurations of samples 400 and thus may be used for such purposes as, for example, determining the volume of a cylindrical compacted field core, modeling the roughness or texture of a surface, obtaining the volume of an excavated void, or gradating components of an asphalt paving mix or aggregate such as size, shape, color, or other configurations.

Figure 3A:
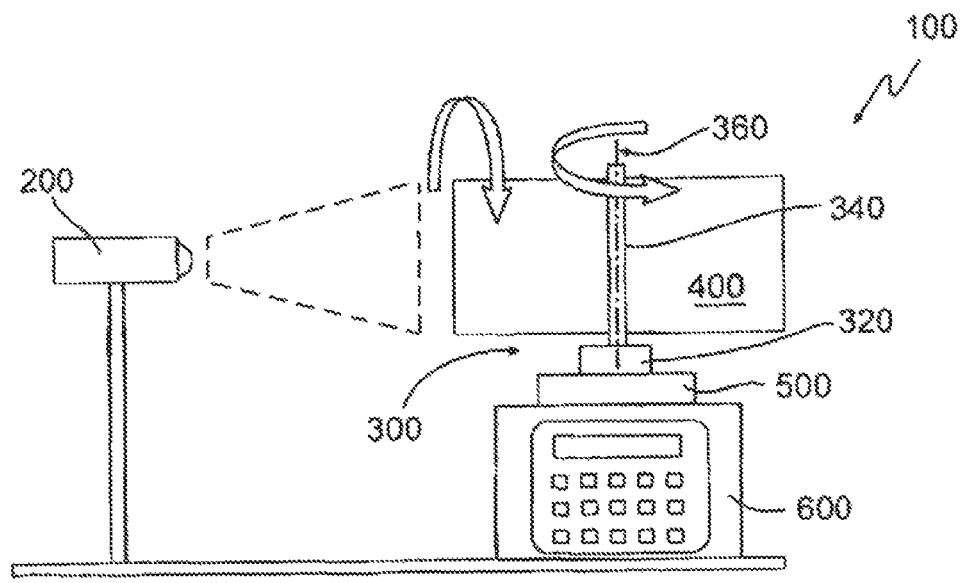
FIGS. 3A and 3B are schematics of an apparatus for determining at least one dimension of a construction material sample, implementing a dimension-measuring device, according to one embodiment of the subject matter disclosed herein in which portion 340 may be optionally used in one or more embodiments.
Figure 3B:
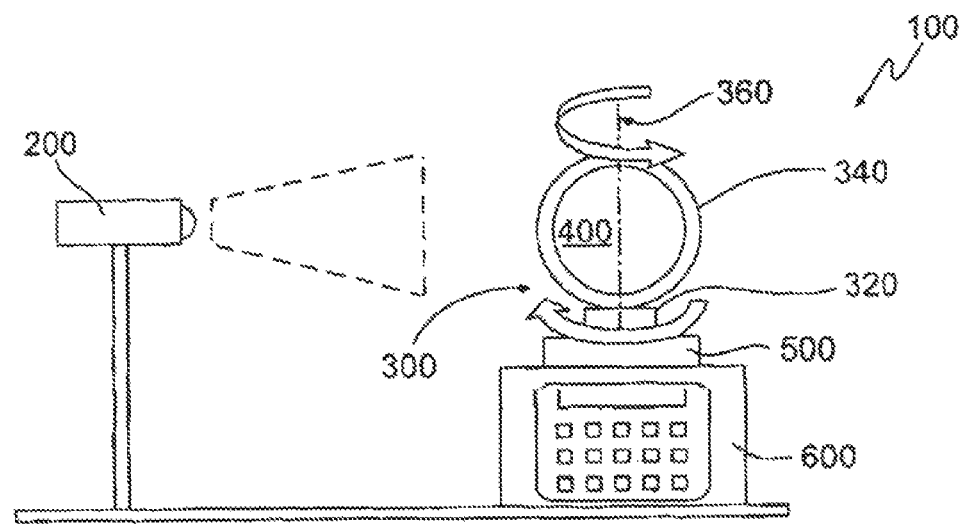

Once a first measurement of sample 400 in a first position is performed by sample-interacting device 200, sample 400 can then be moved to a second position to allow a second measurement of sample 400 to be performed, where such measurements may be associated with, for example, a dimension of sample 400. In such a manner, a more accurate determination of the appropriate surface characteristic(s) of sample 400 can be made so as to enable, for example, the volume of sample 400 to be more closely and accurately determined. Accordingly, in one embodiment as shown in FIGS. 3A and 3B, first and second portions 320, 340 of sample holder 300 define a vertical axis 360 and first and second portions 320, 340 are configured so as to be able to rotate about axis 360 between measurements by sample-interacting device 200. FIGS. 3A and 3B further show sample 400 rotating around axis 360. For example, first and second portions 320, 340 may be configured to rotate in 90-degree increments or 180-degree increments (or any suitable degree increment or even in a continuous sweep) between measurements by sample-interacting device 200, while maintaining sample 400 within the established coordinate system. That is, first and second portions 320, 340 may be configured such that, for instance, a reference point is maintained on first portion 320, second portion 340, and/or sample 400 as sample 400 is rotated about axis 360. Thus, subsequent analysis of the resulting data can use the common reference point in order to reconcile the measured surface characteristic(s) from the particular view of each measurement. Further, multiple measurements of sample 400 from multiple views will also provide redundant data useful for verifying accuracy of the determined surface characteristic(s) of sample 400, thereby providing another significant advantage of embodiments of the subject matter disclosed herein. In some instances, sample-interacting device(s) 200 may be used to perform repeated measurements of sample 400 such that an average of those measurements is used in subsequent analyses of the data. The use of such averages may, in some instances, provide a more accurate representation of the surface characteristic of sample 400 as compared to a single measurement.

Figure 3C:
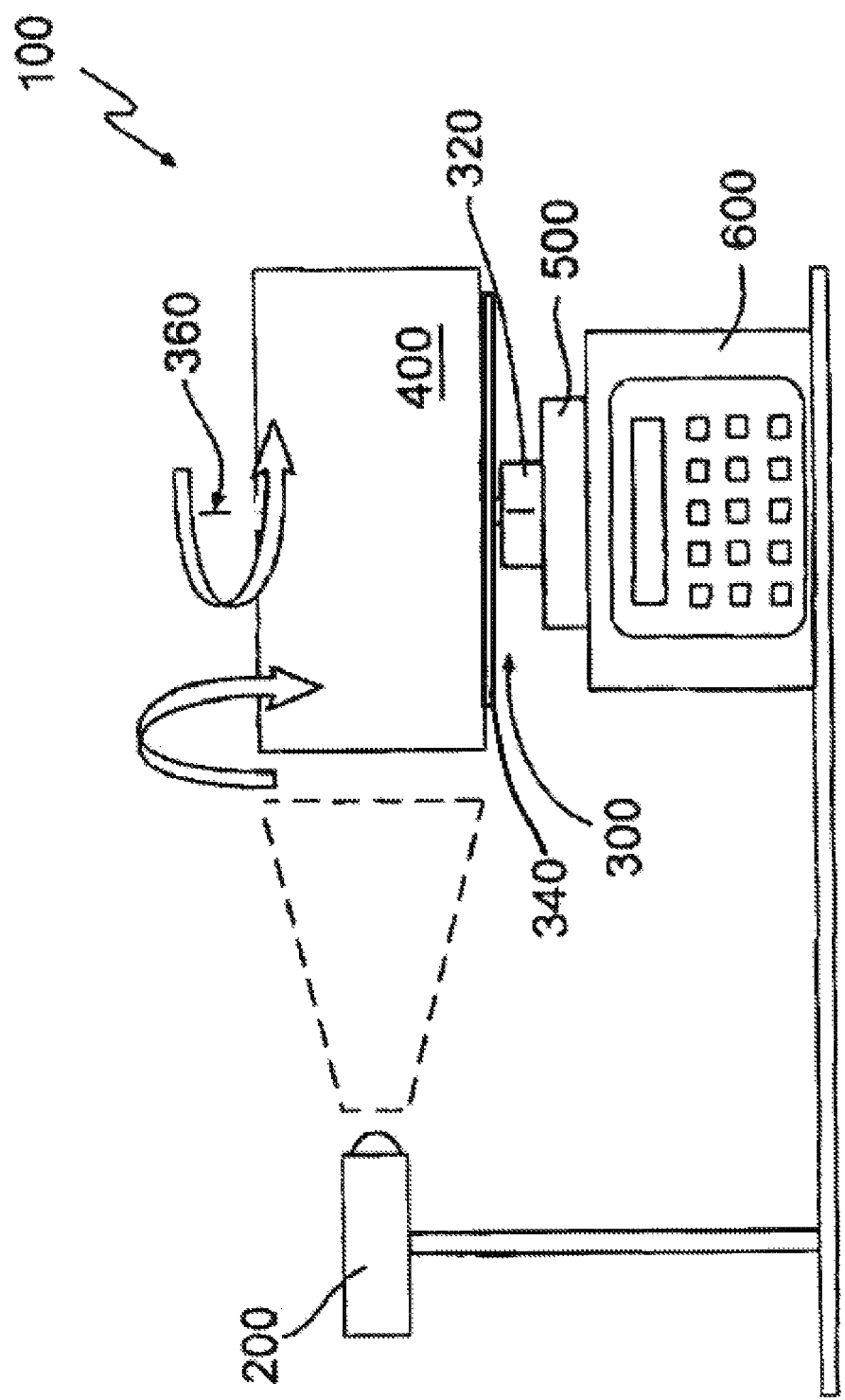
FIG. 3C is a schematic of an apparatus similar to the apparatus depicted in FIGS. 3A and 3B in which the sample holder 340 is not depicted.

In light of the relationship of sample-interacting device 200 to sample 400, as shown in FIGS. 3A, 3B, 3C, 4A, and 4B, other embodiments of the subject matter disclosed herein may be configured such that first and second portions 320, 340 hold sample 400 stationary, while sample-interacting device 200 is configured to move about sample 400 so as to perform the appropriate measurements. In still other instances, both sample-interacting device 200 and sample holder 300 may be movable with respect to each other, or mirrors may be used to enable sample-interacting device 200 to interact with sample 400. Further, other embodiments of the subject matter disclosed herein may have sample holder 300 configured such that second portion 340 is movable with respect to first portion 320 where, for example, first portion 320 may be stationarily disposed with respect to sample-interacting device 200. For a sample holder 300 configured in such a manner, second portion 340 holding sample 400 may be movable in many different manners with respect to first portion 320, as will be appreciated by one skilled in the art. In any instance, such embodiments of apparatus 100 are configured such that sample 400 is maintained in registration with the coordinate system through any movement of sample-interacting device 200 and/or first and/or second portions 320, 340 of sample holder 300. Alternatively, apparatus 100 may be provided without second portion 340 as illustrated in FIG. 3C.

In any case, multiple views and/or measurements or other determinations of the surface characteristic(s) of sample 400 may result in a plurality of representations of sample 400 from different perspectives, wherein the views and/or measurements must then be combined in order to provide coherent and useful results. Where sample 400 and/or sample-interacting device 200 must be moved, or multiple perspectives of sample 400 are obtained, in order to provide three-dimensional surface characteristics of sample 400, the software executed by computer device 600, in cooperation with sample-interacting device 200, may be configured to determine a coordinate system or other frame of reference for the various measurements or determinations of the surface characteristic(s) of sample 400 performed by sample-interacting device 200. For example, the frame of reference may be designated, for example, at least partially according to sample holder 300 or according to a surface aspect or feature of sample 400, such as a void or other irregularity. In other instances, the frame of reference may be artificial, such as a mark or other removable (or inconsequential) surface feature added to sample 400 prior to exposure to sample-interacting device 200. As such, once a sufficient number of source-associated measurements have been executed, the various perspectives 650 of sample 400 obtained by sample-interacting device(s) 200, as shown in FIG. 2B (where FIG. 2B illustrates the plurality of perspectives of the sample 400 captured by the corresponding plurality of sample-interacting devices 200 shown in FIG. 2A), can be combined or "stitched together" according to the coordinate system or other frame of reference into a single three-dimensional representation or model 700 of sample 400.

Figure 4B:
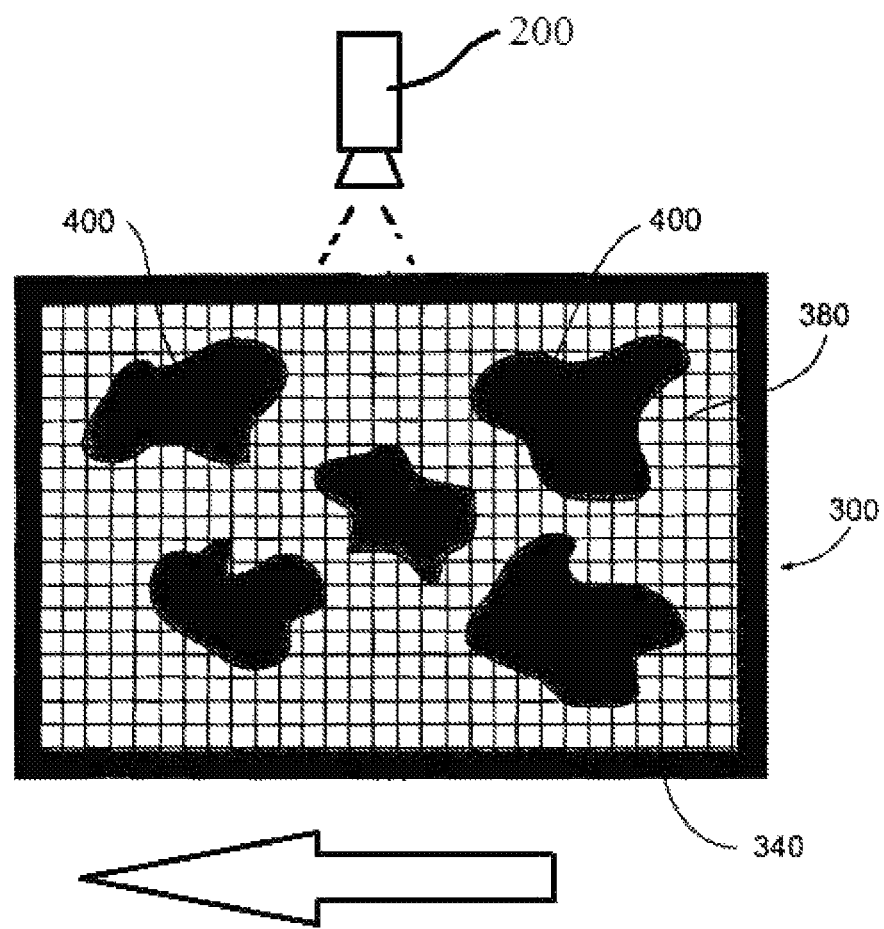
Figure 5:
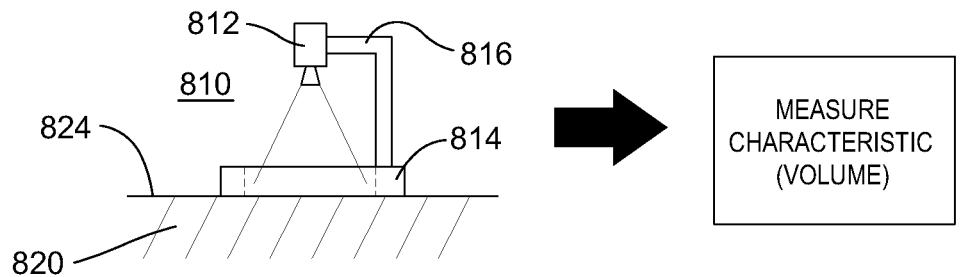
FIG. 5 is a schematic view of an apparatus for determining a volume of a construction material according to one embodiment of the subject matter disclosed herein in which an imaging device is spaced-apart from a construction material.
Figure 6:
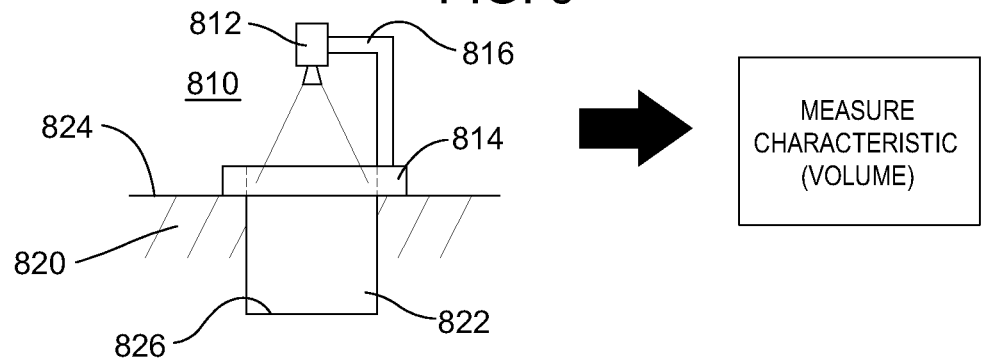
FIG. 6 is a schematic view of an apparatus for determining a volume of a construction material according to one embodiment of the subject matter disclosed herein in which an imaging device is spaced-apart from a void in a construction material.

FIG. 4B is a schematic of an alternate sample holder 300 for an apparatus for determining at least one dimension of a construction material sample holder similar to the sample holder depicted in FIG. 4A in which the sample holder 300 is translating relative to an imaging device according to one embodiment of the subject matter disclosed herein. A directional arrow is provided to signify moving of the sample holder 300, such as, for example, movement of a conveyor line on which the construction material is resting. Accordingly, imaging device 200 can be proximal to sample holder 300, in this illustrative example, a conveyor line, and interact with the sample to determine characteristics thereof, including height, aggregate size, density, color, shape, texture, or other desired properties and characteristics.

One skilled in the art will thus appreciate that apparatus 100 may be configured in many different manners in addition to that described herein. For example, apparatus 100 may include multiple sample-interacting or dimension-measuring devices 200, each disposed to provide different perspectives of the sample 400, or one or more sample-interacting devices 200 may each include multiple sources and/or detectors. In addition, various other mechanisms, such as mirrors, could be implemented to facilitate the determination of the desired surface characteristic(s) of sample 400. Thus, the embodiments disclosed herein are provided for example only and are not intended to be limiting, restrictive, or inclusive with respect to the range of contemplated configurations of the subject matter disclosed herein.

According to a further advantageous aspect of the subject matter disclosed herein, apparatus 100 may also be configured such that sample-interacting device 200 and/or computer device 600 is capable of determining the volume of sample 400. One value often associated with the determination of the volume of sample 400 is the density thereof. As previously described, the general procedures heretofore implemented by recognized standards in the construction industry are often, for instance, cumbersome, inaccurate, or destructive to sample 400. As such, in some instances, embodiments of the subject matter disclosed herein may also include a mass-determining device 500 operably engaged with sample holder 300 such that, as the volume of the sample 400 is being determined by the sample-interacting device 200, mass of the sample 400 can also be determined concurrently. The density of sample 400 can thereby be expeditiously determined with minimal handling of the sample 400. Such a mass-determining device 500 may comprise, for example, a load cell or other suitable device as will be appreciated by one skilled in the art. In still other instances, it may also be advantageous for the determination of the volume and/or the density of sample 400 by the apparatus 100 to be at least partially automated so as to reduce the subjectivity of handling by an operator. Accordingly, in such instances, apparatus 100 may also include a computer device 600 operably engaged with the sample-interacting device 200, mass-determining device 500, and/or sample holder 300. Such a computer device 600 may be configured to, for instance, verify that sample 400 is properly placed with respect to sample holder 300 and/or the sample-interacting device 200, coordinate the movement of sample 400 with the measurements performed by sample-interacting device 200, determine the mass of sample 400 from mass-determining device 500, and compute the density of sample 400 all in one automated procedure. Computer device 600 may also be configured to perform other procedures on the collected sample data that may be of further interest. For example, computer device 600 may be configured to compute the volume of sample 400 from a complex integration of a three-dimensional surface image of the sample 400 and/or may be configured to determine an actual volume of the sample 400 by determining the effect of surface voids or roughness in sample 400 along with boundary locations and dimensions. Computer device 600 may also vary in complexity depending on the computational requirements of apparatus 100. For example, an image-intensive apparatus 100 using a plurality of sample-interacting devices 200 may require a significant capacity and an image-capable computer device 600, while a less complex dimension-determining may require less computational capacity and, in light of such requirements, an appropriate computer device 600 is provided. Thus, one skilled in the art will appreciate that embodiments of the apparatus 100 may be used for many other forms of sample analysis in addition to those discussed herein.

Many modifications and other embodiments of the subject matter disclosed herein will come to mind to one skilled in the art to which the subject matter disclosed herein pertains having the benefit of the teachings presented in the foregoing descriptions and the associated drawings. For example, one skilled in the art will appreciate that the apparatus and method as disclosed and described herein, in addition to providing an alternative to the density determination methodology outlined in the applicable density standards, may also be implemented within the methodology of other higher-level standards that call, for instance, for the determination of sample density using those density standards, or for the determination of sample dimensions such as, for example, a histogram of aggregate sizes. For example, several AASHTO/ASTM standards are directed to aggregate gradation and may specify the determination of an aggregate size histogram, wherein the apparatus and method as disclosed and described herein may be implemented to make that determination. Such standards include, for instance:

AASHTO T 27 Sieve Analysis of Fine and Coarse Aggregates; AASHTO T 30 Mechanical Analysis of Extracted Aggregate;

AASHTO MP 2 Standard Specification for SUPERPAVE Volumetric Mix Design;

AASHTO T 312 Method for Preparing and Determining the Density or HMA Specimens by Means of the SHRP Gyratory Compactor;

ASTM C 136 Sieve Analysis of Fine and Coarse Aggregates;

ASTM D 5444 Test Method for Mechanical Size Analysis of Extracted Aggregate;

ASTM D 3398 Test Method for Index of Aggregate Particle Shape and Texture;

ASTM D 2940 Specification for Graded Aggregate Material For Bases or Subbases for Highways or Airports;

ASTM D 448 Classification for Sizes of Aggregate for Road and Bridge Construction; and ASTM D 1139 Standard Specification for Aggregate for Single and Multiple Bituminous Surface Treatments.

Note that such a list is merely exemplary of some standards for aggregates in which aggregate gradation may be specified, and is not intended to be limiting, restrictive, or inclusive with respect to such higher-level standards which may specify a dimension, volume, density, and/or other sample property determination that may be accomplished using the apparatus and method as disclosed and described herein. Accordingly, additional embodiments of the subject matter disclosed herein may be directed to such higher level methods implementing the apparatus and method as disclosed herein. Further, other additional embodiments of the subject matter disclosed herein may, for example, be used to determine the texture of a sample. Some examples of ASTM standards requiring an examination of the sample texture, wherein the apparatus and method as disclosed and described herein may also be implemented to make that determination, include:

ASTM E 965 Standard Test Method for Measuring Pavement Macro Texture Depth Using a Volumetric Technique;

ASTM E 1274 Standard Test Method for Measuring Pavement Roughness Using a Profilograph; and ASTM E 2157 Standard Test Method for Measuring Pavement Macro Texture Properties Using the Circular Track Method.

Additionally, the following ASTM standards may be employed with the use of the disclosed subject matter contained herein:

ASTM D6432-99(2005) Standard Guide for Using the Surface Ground Penetrating Radar Method for Subsurface Investigation;

ASTM D6431-99(2010) Standard Guide for Using the Direct Current Resistivity Method for Subsurface Investigation;

ASTM D6565-00(2005) Standard Test Method for Determination of Water (Moisture) Content of Soil by the Time-Domain Reflectometry (TDR) Method;

ASTM D6639-01(2008) Standard Guide for Using the Frequency Domain Electromagnetic Method for Subsurface Investigations;

ASTM D6780-05 Standard Test Method for Water Content and Density of Soil in Place by Time Domain Reflectometry (TDR);

ASTM D6820-02(2007) Standard Guide for Use of the Time Domain Electromagnetic Method for Subsurface Investigation;

Historical Standard: ASTM D2216-98 Standard Test Method for Laboratory Determination of Water (Moisture) Content of Soil and Rock by Mass;

ASTM D4643-08 Standard Test Method for Determination of Water (Moisture) Content of Soil by Microwave Oven Heating;

ASTM D4944-04 Standard Test Method for Field Determination of Water (Moisture) Content of Soil by the Calcium Carbide Gas Pressure Tester;

ASTM D4959-07 Standard Test Method for Determination of Water (Moisture) Content of Soil By Direct Heating;

ASTM D5030-04 Standard Test Method for Density of Soil and Rock in Place by the Water Replacement Method in a Test Pit;

ASTM D5080-08 Standard Test Method for Rapid Determination of Percent Compaction;

ASTM D2167-08 Standard Test Method for Density and Unit Weight of Soil in Place by the Rubber Balloon Method;

ASTM D2974-07a Standard Test Methods for Moisture, Ash, and Organic Matter of Peat and Other Organic Soils;

ASTM D4254-00(2006)e1 Standard Test Methods for Minimum Index Density and Unit Weight of Soils and Calculation of Relative Density;

ASTM D6938-10 Standard Test Method for In-Place Density and Water Content of Soil and Soil-Aggregate by Nuclear Methods (Shallow Depth);

ASTM D425-88(2008) Standard Test Method for Centrifuge Moisture Equivalent of Soils;

ASTM D6642-01(2006) Standard Guide for Comparison of Techniques to Quantify the Soil-Water (Moisture) Flux;

ASTM D558-11 Standard Test Methods for Moisture-Density (Unit Weight) Relations of Soil-Cement Mixtures;

ASTM D 1556—Test Method for Density of Soil in Place of the Sand-Cone Method;

ASTM C127-04 Standard Test Method for Density, Relative Density (Specific Gravity), and Absorption of Coarse Aggregate;

ASTM D4791-10 Standard Test Method for Flat Particles, Elongated Particles, or Flat and Elongated Particles in Coarse Aggregate;

ASTM C29/C29M-09 Standard Test Method for Bulk Density (Unit Weight) and Voids in Aggregate;

ASTM D2940/D2940M-09 Standard Specification for Graded Aggregate Material For Bases or Subbases for Highways or Airports;

ASTM D3398-00(2006) Standard Test Method for Index of Aggregate Particle Shape and Texture;

ASTM D448-08 Standard Classification for Sizes of Aggregate for Road and Bridge Construction;

ASTM C70-06 Standard Test Method for Surface Moisture in Fine Aggregate;

ASTM D1241-07 Standard Specification for Materials for Soil Aggregate Subbase, Base, and Surface Courses;

ASTM D692/D692M-09 Standard Specification for Coarse Aggregate for Bituminous Paving Mixtures;

ASTM D3282-09 Standard Practice for Classification of Soils and Soil Aggregate Mixtures for Highway Construction Purposes;

ASTM C925-09 Standard Guide for Precision Electroformed Wet Sieve Analysis of Nonplastic Ceramic Powders; and ASTM D6913-04(2009) Standard Test Methods for Particle Size Distribution (Gradation) of Soils Using Sieve Analysis.

An alternate embodiment of an apparatus for measuring a characteristic of a construction material is depicted in FIGS. 5 through 8 in which an apparatus 810 is provided. The apparatus 810 generally defines a material-interacting device 812, which may have many of the same characteristics and capabilities of material-interacting devices described throughout this disclosure. The material-interacting device 812 may be carried by a frame 816 that may extend from a template 814. The template 814 and frame 816 cooperate to carry the material-interacting device 812 and may be configured for translating the material-interacting device 812 in any desired direction through the use of a geared linkage, motor, step motor, optical, or any other desired translation method. This translation may be provided, for example, for positioning the material-interacting device 812 in a certain proximity or position relative to a material to be interacted with. In other embodiments, this translation may be provided, for example, for positioning the material-interacting device 812 among a plurality of positions in order to interact with the material among multiple positions. Alternatively, a system may be provided in which a plurality of translatable mirror assemblies are provided for capturing multiple images and interactions with the material-interacting devices disclosed herein.

The template 814 may be provided for being positioned against a surface 824 of a construction material 820. In this manner, the template 812 may provide leveling characteristics and positioning characteristics such that the material-interacting device 812 is in a desired position or orientation. A void 822 may be formed in the construction material 820 by, for example, excavating the construction material 820 to form the void 822. The void 822 may include surface 826. The void 822 may be an excavated hole in which a construction material sample has been excavated to determine the density or other desired characteristics thereof.

Figure 7:
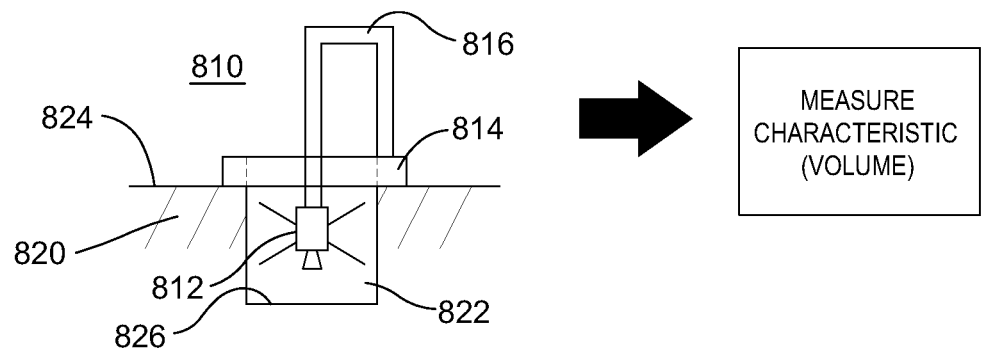
FIG. 7 is a schematic view of an apparatus for determining a volume of a construction material according to one embodiment of the subject matter disclosed herein in which the imaging device has been translated to within the void in the construction material.
Figure 8:
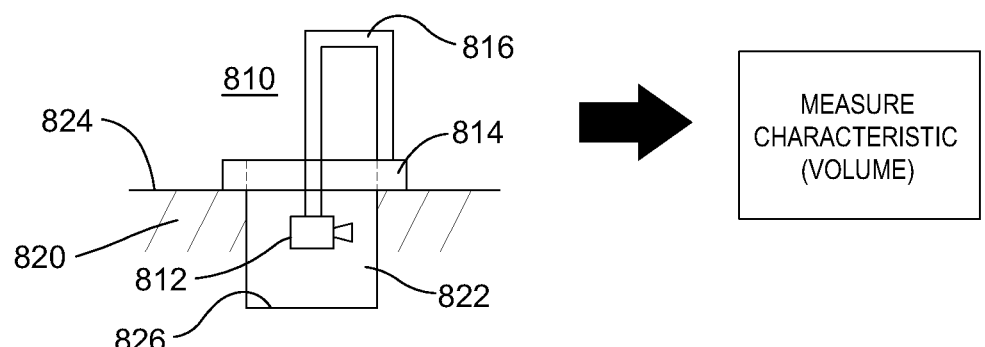
FIG. 8 is a schematic view of an apparatus for determining a volume of a construction material according to one embodiment of the subject matter disclosed herein in which the imaging device has been translated to within the void in the construction material and capturing images within the void.

The material-interacting device 812 is further configured to determine a characteristic of the void 822, while, in one or more embodiments, the material-interacting device 812 may be in communication with an external device such as a computer device that is configured to determine a characteristic of the void. This characteristic may include any characteristic as described herein, and, in one or more embodiments, may include the volume of the excavated void 822, the depth, width, color, surface area, texture, and/or moisture content, and combinations thereof. The material-interacting device 812 may be configured for being received within the void 822 such as depicted in FIG. 7, and may also be configured for being rotationally received within the void 822 as depicted in FIG. 8. However, the material interactive device 812 is not required to be placed within the void 822 to calculate a characteristic thereof, and may be placed outside of the void 822. In one or more embodiments, the material-interacting device 812 may be configured for horizontal, vertical, or rotational movement within the void 822. Other methods may incorporate a plurality of laser sources, reflective surfaces, and optical scanners to scan the void while minimizing the number of sources, detectors and carriage movement.

In one or more embodiments, the material-interacting device 812 may be further configured to interact with other optical devices such as mirrors, detectors, couplers, splitters, polarizers, modulators, photo-emitters, photo-detectors, fibers, waveguides, and lights in order to interact with the material. Additionally, the material-interacting device 812 may include multiple sensors or multiple optical devices operating at multiple wavelengths. The material-interacting device 812 may also employ one or more stereo vision techniques, including capturing multiple images from respective different angles relative to the construction material 820.

Figure 9:
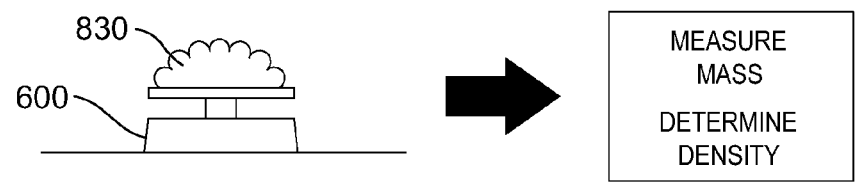
FIG. 9 is a schematic view of a scale for determining the mass of a construction material. The scale may be provided in communication with a computing device or similar for further manipulation of data.

The material-interacting device 812 may be configured for determining a volume of the void 822 formed in the construction material 820. The void 822 is formed by excavating material from the construction material 820, which may be, in one embodiment, soil removed from a road bed or other ground surface. In one method, a template is anchored or fastened to the ground, which offers a guide for excavating the construction material, and allows quick attachment and release of the optical profiler for measuring the hole. The excavated material is depicted in FIG. 9 and represented as 830. The excavated material 830 may be provided on the mass determining device 600, which may then determine the mass of the excavated material 830. Once the mass is obtained by the mass determining device 600, which may be in communication with the material-interacting device, and the volume is obtained by the material-interacting device 812, a density can be obtained. This density represents the density of, in this illustrating example, the soil forming void 822 before being excavated from the ground.

Further testing and calculations can be performed on the excavated material 830 such as determining the "wet" density, and then determining the "dry" density after the excavated material 830 has been dried. Alternate methods of moisture measurement may be implemented such as infrared (IR) measurements, capacitance, electromagnetic, or any other ASTM method provided herein.

The advantages associated with apparatus 810 are readily apparent. For example, apparatus 810 may be portable and can therefore perform in-situ site analysis. This is important for speed and practicality purposes. Conventional methods utilizing the sand cone and rubber balloon methods required many measuring devices, were time consuming, and had limited effectiveness in measurement accuracy. Apparatus 810 is configured such that, operating alone, the volume of an excavated void can be determined.

Figure 10:
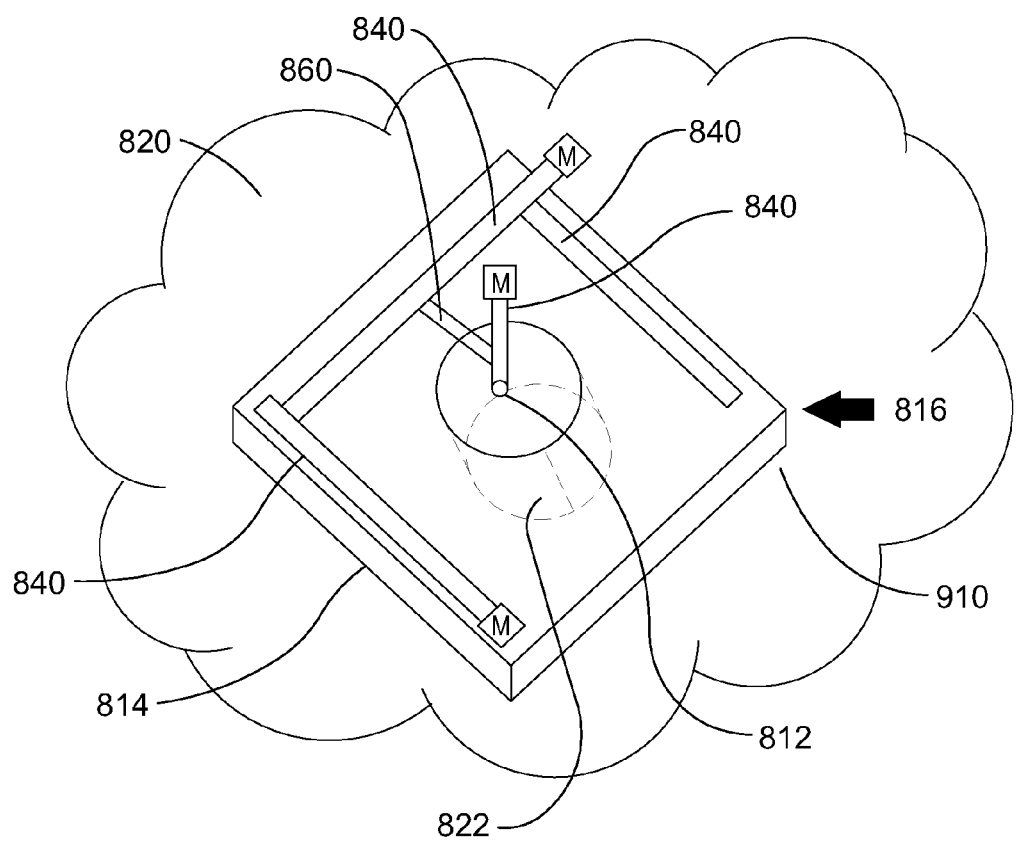
FIG. 10 is a perspective view of an apparatus placed on a planar surface for determining a volume of an excavated void dug in a construction material according to one embodiment of the subject matter disclosed herein.

An apparatus for determining a characteristic of a construction material is depicted in FIG. 10 and is generally designated 910. The apparatus 910 includes a material-interacting device 812 that is carried by a frame structure 816 that includes at least one translation device 840. Drive beams 840 may be provided with a threaded, notched, or similar configuration that receives mechanical input from a device such as a motor "M" for varying the position of the material-interacting device 812. Template 814 carries each of the drive beams 840. A boom 860 may extend from one of the drive beams for carrying a vertically oriented drive beam. Template 814 is configured for being placed on the construction material 820. The material-interacting device 812 is configured for interacting with the construction material and further configured for interacting with the void 822 defined in the construction material. The material-interacting device 812 is further configured for movement in up to, for example, three dimensions within the void 822. Optical systems and components such as couplers, splitters, and dynamic or static mirrors may be substituted for direct mechanical positioning of the relationship between the interacting device and sample.

Figure 11:
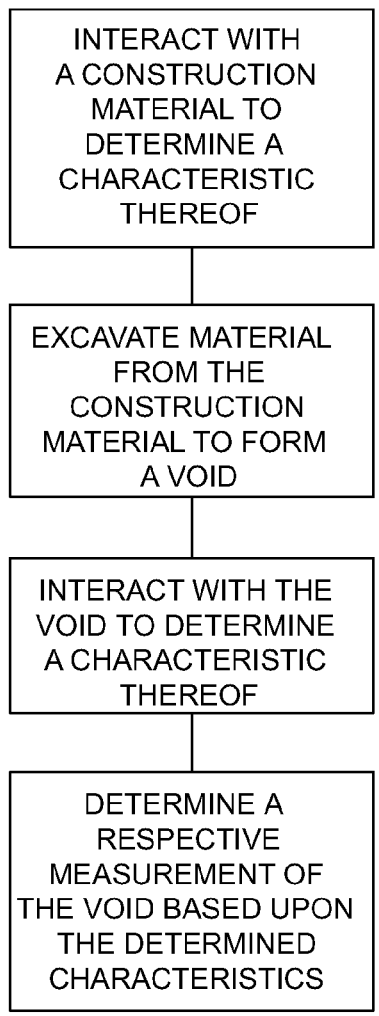
FIG. 11 is a flow chart depicting a method disclosed herein.

A method 1100 is depicted in the flow chart of FIG. 11. The method 1100 may generally include interacting with a construction material to determine a characteristic thereof, excavating material from the construction material to form a void, interacting with the void to determine a characteristic thereof, and determining a respective measurement of the void based upon the determined characteristics. The interaction may include, for example, forming a first image before excavation, forming a second image after excavation, the second image being that of the void, and determining a measurement of the void based upon the determined images. This measurement may be, for example, the volume of the void. Conversely, one image can be obtained of the void for calculating the void volume, though an image is not required.

Figure 12:
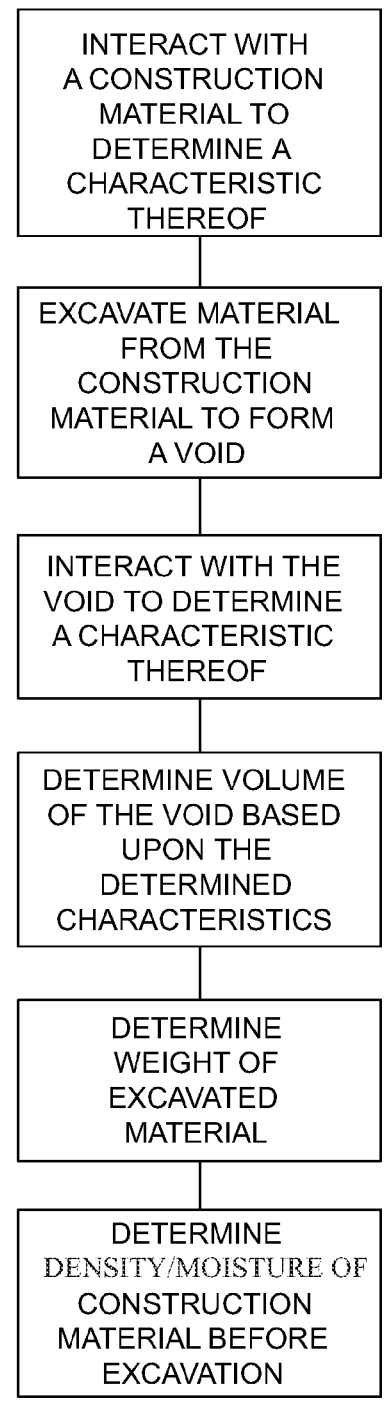
FIG. 12 is a flow chart depicting a method disclosed herein.

A method 1200 is depicted in the flow chart of FIG. 12. The method 1200 may generally include interacting with a construction material to determine a characteristic thereof, excavating material from the construction material to form a void, interacting with the void to determine a characteristic thereof, and determining the volume of the void based upon the desired characteristics. Further, the method 1200 may include determining the weight (mass) of the excavated material, and then determining the density of the construction material in-situ, as it was before excavation. This density may be found, for example, by dividing the mass by the volume of the void.

Figure 13:
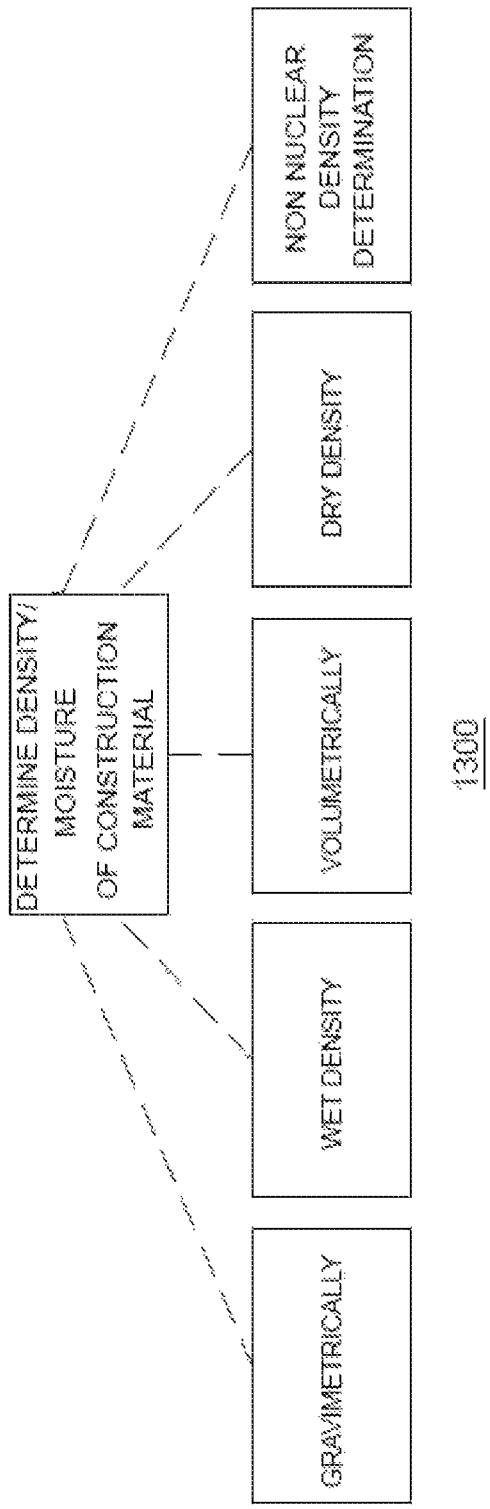
FIG. 13 is a flow chart depicting a method for determining the density and/or moisture of a construction material.

Determining the density of the construction material may be accomplished in any number of ways, including those depicted in the method 1300 of FIG. 13. Determining the density or moisture content may include determining the wet density. Determining the density may also include determining a dry density using non-nuclear moisture determination methods. Determining the density may also include determining the density volumetrically. Determining the density may also include determining the density and moisture by gravimetrical methods. Determining the density may also include determining the dry density using methods by, for example, heating the soil to remove moisture.

Figure 14:
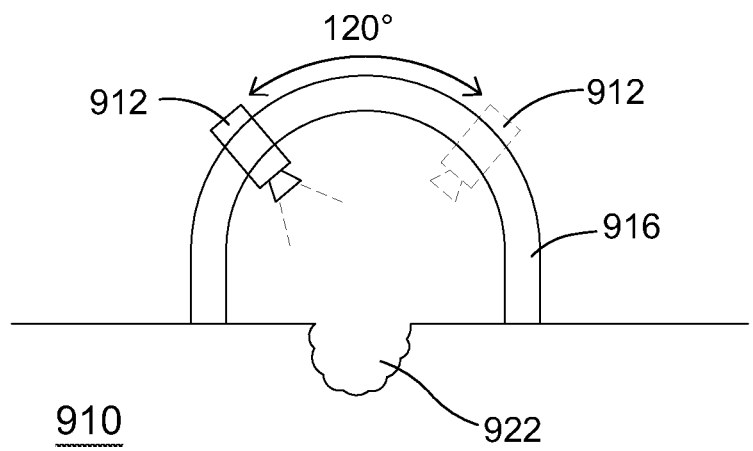
FIG. 14 is a side view of an apparatus for determining a volume of a construction material according to one embodiment of the subject matter disclosed herein in which a single lens is illustrated in a structure capable of consistently obtaining multiple angle Images. Alternatively, a standard multi-lens system may be incorporated.

An apparatus 910 is illustrated in FIG. 14. The apparatus 910 includes an imaging device 912 or material-interacting device 912 carried by a frame 916. The frame 916 is depicted as having an arcuate shape, but may take on any appropriately configured shape. The frame 916 is configured for being positioned about a construction material surface, such as, for example, a road surface. A void 922 or other deviation may be formed in the surface. Imaging device 912 may be translatable from a first position (in which the imaging device 912 is shown in solid lines) to a second position (in which the imaging device 912 is shown in broken lines). The imaging device 912 may also have more than two positions. Alternatively, the frame 916 may carry multiple imaging device 912 such that translation of the imaging device 912 is not required to obtain multiple images for use with, for example, stereographic imaging or other imaging methods described herein. The imaging device 912 is configured to determine one or more measurements to thereby determine one or more characteristics of void 922 or other suitable deviations using the one or more processes described herein. FIG. 14 shows an angle of separation between the respective imaging device 912 in the first and second positions of about 120 degrees, however any appropriate angle may be incorporated for the image analysis.

Figure 15:
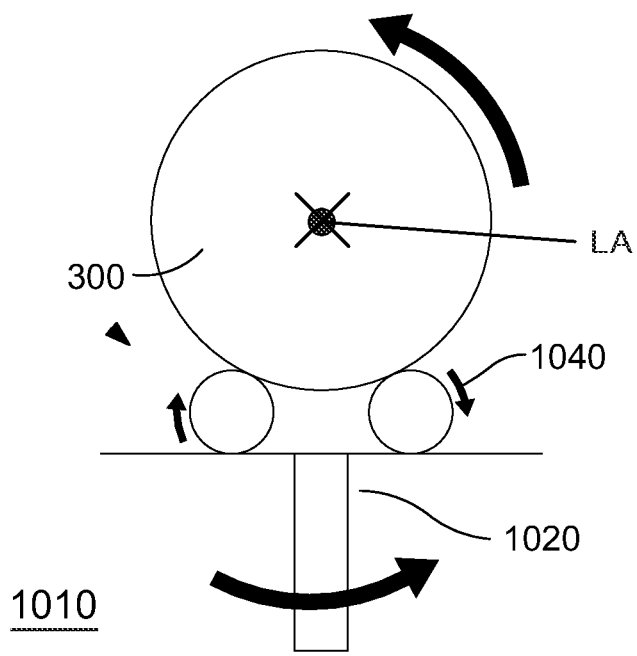
FIG. 15 is a side view of an apparatus for carrying a construction material according to one embodiment of the subject matter disclosed herein.
Figure 16:
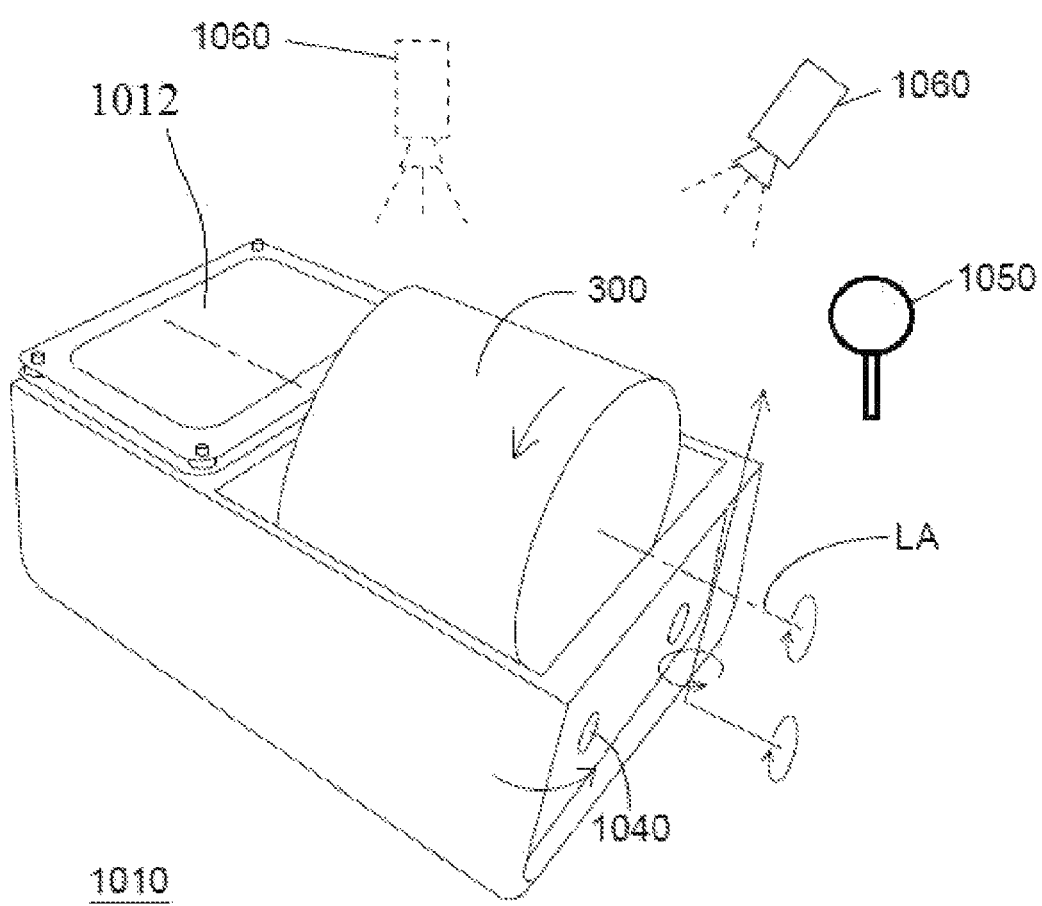
FIG. 16 is a perspective view of an apparatus for carrying a construction material according to one embodiment of the subject matter disclosed herein.

An apparatus that may be used in accordance with embodiments described herein is shown in FIGS. 15 and 16 and is generally designated 1010. The apparatus 1010 may include at least one translation mechanism 1040, which may be a roller as illustrated or may be any other desired mechanism capable of translating the construction material sample 300. The construction material sample 300 defines a longitudinal axis "LA" about which the construction material sample 300 is rotated by the translation mechanisms 1040. Each of the arrows are provided in the illustrations to depict the translation movement of the translation mechanism 1040 and the imparted movement of the construction material sample 300 in response thereto. One or more additional translation mechanisms 1020 may also be provided for translating the construction material sample 300 in a yaw, pitch, roll, or similar orientation. A housing 1012 may be provided for receiving the construction material sample 300 and housing the translation mechanisms 1040 as illustrated in FIG. 16.

As illustrated in FIG. 16, a light source 1050 may be provided. The light source 1050 may be a light point, a light line, laser source, coherent light, or a wave front, or any other suitably configured device for interacting with the construction material sample 300. A material-interacting device 1060 may be further provided. The material-interacting device 1060 may be provided in a fixed-relationship relative to the construction material sample 300. Alternatively, the material-interacting device 1060 may be translatable from a first position (in which the material-interacting device 1060 is shown in solid lines) to a second position (in which the material-interacting device 1060 is shown in broken lines). Alternatively, multiple material-interacting devices 1060 in variously selected positions may be employed. When the translation mechanism 1040 is actuated so that the construction material sample 300 is rotated, the material-interacting device 1060 captures multiple readings of the construction material sample 300. In this manner, one or more characteristics such as density, volume, and the like as described with reference to the apparatuses, devices, and methods described herein can be determined by the material-interacting device 1060.

Figure 17:
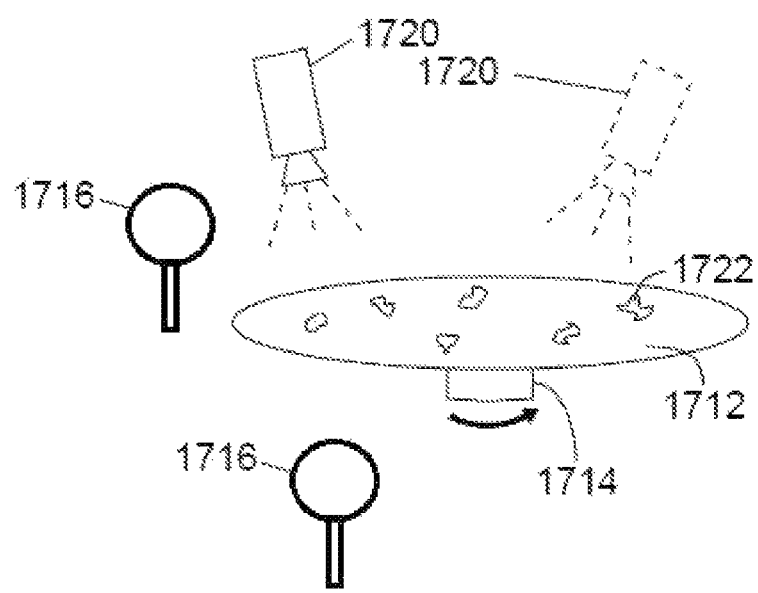
FIG. 17 is a perspective view of an apparatus for interacting with a construction material according to one embodiment of the subject matter disclosed herein.

An apparatus for measuring and determining characteristics of a construction material sample according to one or more embodiments is illustrated in FIG. 17 and generally designated 1710. The apparatus 1710 includes a panel 1712 that is translatable about a translation mechanism 1714. A light source 1716 may be provided, and multiple light sources 1716 are illustrated in FIG. 17. The light source 1716 may be a light point, a light line, laser source, coherent light, or a wave front. A material-interacting device 1720 may be provided. The material-interacting device 1720 may be provided in a fixed-relationship relative to a construction material 1722 provided on the panel 1712. Alternatively, the material-interacting device 1720 may be translatable from a first position (in which the material-interacting device 1720 is shown in solid lines) to a second position (in which the material-interacting device 1720 is shown in broken lines). Alternatively, multiple material-interacting devices 1720 in variously selected positions may be employed. When the translation mechanism 1714 is actuated so that the panel 1712 is rotated, the material-interacting device 1720 captures multiple readings of the construction material samples 1722. In this manner, one or more characteristics such as density, volume, shape, texture, angularity, size, and the like as described with reference to the apparatuses, devices, and methods described herein can be determined by the material-interacting device 1720. A histogram based on these values can be obtained such that an "optical sieve" is developed.

Figure 18:
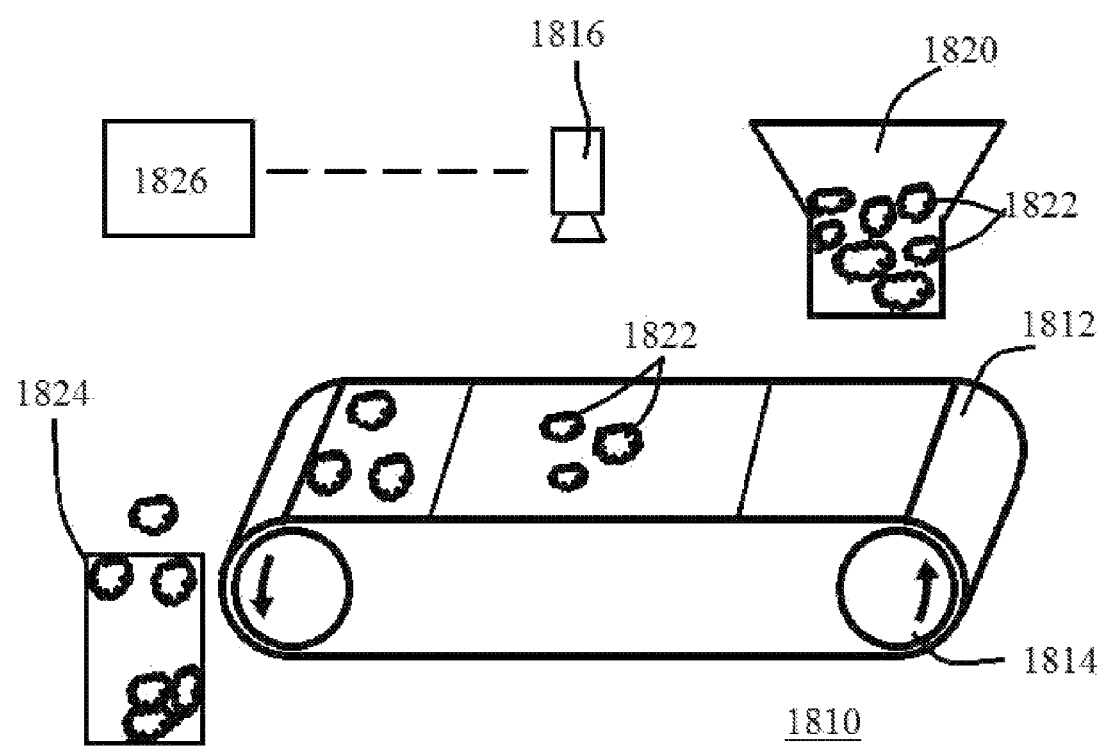
FIG. 18 is a perspective view of a system and apparatus for determining a characteristic of a construction material.

A system for measuring and determining characteristics of a construction material sample according to one or more embodiments is illustrated in FIG. 18 and generally designated 1810. The system 1810 includes a conveyor-type assembly 1812. Conveyor assembly 1812 may be unidirectional, bi-directional, or configured for alternating between directional movements. The conveyor assembly 1812 may be translated by a roller wheel assembly 1814 or any other desired apparatus. A material-interacting device 1816 similar to other material-interacting devices disclosed herein may be provided in any position relative to the conveyor assembly 1812. Additionally, more than one material-interacting device 1816 may be employed. A hopper system 1820 or similar device for dispensing construction material samples 1822 onto the conveyor assembly 1812 may be provided. The construction material sample 1824 may translate with the conveyor assembly into a mixer, a cart or storage bin 1824 as illustrated. The material-interacting device 1816 may be provided in communication with a computing device 1826 for further manipulation of data captured by the material-interacting device 1816. The material-interacting device 1816 may determine one or more characteristics such as density, volume, height, thickness, angularity, size, shape, texture and the like. Material-interacting device 1816 may be an optical scanning device, or, alternatively, an ultrasonic device or any other device disclosed herein. It may operate in a reflection mode or a transmission mode, sometimes referred to as a pitch and catch mode.

Figure 19:
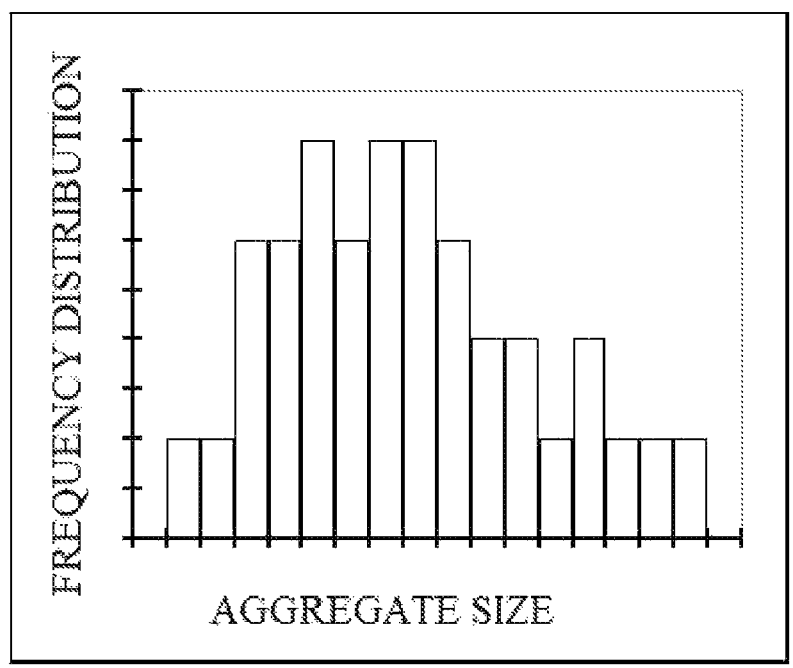
FIG. 19 is a histogram representing characteristics of a construction material according to one embodiment of the subject matter disclosed herein.

The material-interacting device 1816 and computing device 1826 may be operably configured for creating a histogram or other statistical compilation of the one or more determined characteristics. For example, a histogram illustrated in FIG. 19 may illustrate aggregate size as a function of frequency as determined by the material-interacting device 1816 and computing device 1826. Other characteristics may also be represented with a histogram similar to that which is illustrated in FIG. 19.

Other ASTM and AASHTO methods and standards may also be employed. Additional methods may be found in the Asphalt Institute Soils Manual MS-10 and a publication entitled "CONVENTIONAL DENSITY TESTING" printed by the North Carolina Department of Transportation, both publications of which are hereby incorporated by reference. Other methods may be found in the North Carolina Department of Transportation manual entitled "AGGREGATE BASE COUSE NUCLEAR DENSITY TESTING MANUAL" by Jim Sawyer and printed by the North Carolina Department of Transportation published Jun. 4, 2003, the contents of which are hereby incorporated by reference. Other methods may be found in the North Carolina Department of Transportation manual entitled "CONVENTIONAL DENSITY OPERATOR'S MANUAL" by Levi Regalado, edited by Jim Sawyer, and printed by the North Carolina Department of Transportation and published on Aug. 16, 2002, and revised on Oct. 11, 2004, the contents of which are hereby incorporated by reference.

Additionally, methods of determining the moisture content of a sample of material excavated from a void may be employed. For example, methods of determining a moisture content are disclosed in U.S. Pat. Nos. 7,239,150, 7,569,810, and 7,820,960, the entire contents of which are hereby incorporated by reference.

U.S. Pat. Nos. 7,239,150, 7,569,810, 7,581,446 and 7,820,960 disclose many methods of determining a moisture content, as well as methods for preparing soil or other material for testing, all of which are hereby incorporated by reference in their entirety. Including and in addition to those patents, manners of determining a moisture content may include direct heating, time-domain reflectometry (TDR), capacitive measurements including swept frequency capacitance, microwave heating, microwave impedance, calcium carbide meters known as "Speedy" meters, electromagnetic methods, magnetic resonance, and ground penetrating radar (GPR) techniques.

The following examples are illustrative of processes that may be employed with one or more apparatuses or devices disclosed herein.

As used herein, the term "squeeze" method is used for obtaining an idea of how close the soil is to optimum moisture content. The squeeze method may be for determining the optimum moisture of a soil mass and can be performed by an experienced technician with acceptable accuracy. The squeeze method may work well with cohesive soil.

Any lumps and clods in the excavated soil material should be pulverized. The mass of soil should be mixed and fairly homogeneous. In the method, a handful of loose soil is taken in one hand of the operator and firmly squeezed into an elongated mass. The moisture is close to optimum moisture if:
1. The mass exhibits cohesion. The soil should not break apart after releasing the soil from the hand after squeezing. If the soil does break apart, the user should add a small bit of water if the test calls for obtaining optimum moisture.
2. Remains cohesive under stress. The user throws the mass of soil up in the air 4 or 6 inches high and catches the mass on descent. If the mass remains intact, the mass is close to optimum cohesiveness. If not, the user should add water if necessary to obtain optimum moisture.
3. There is coolness of the palm. The user should feel a coolness in their palm when handling the soil, but there should be no visible moisture left in the user's hand upon releasing the soil.
4. The penny print. During compaction using a mold compactor, if, at the end of the compaction, the ram rod should be cleaned and then struck in the middle of the mold. If the imprint left by the ram rod is a depth of about 1-2 mm deep, about the thickness of a penny, then it is close to optimum moisture. If a full print of the ram rod cannot be seen, then the soil is too dry.

These criteria are true even if the mass is above optimum moisture. If it is above optimum, a noticeable film of moisture will appear on the hand, also leaving some of the dirt behind as well. In this case, the soil should be slowly dried in air if optimum moisture is required.

In the following examples, the density of a soil base will be measured using methods and one or more apparatuses described herein to optically determine the volume of an excavated void in the soil, sub-base, ground and calculate the wet or dry density by weighing the excavated mass from the void.

Example 1

In this example, embankments and subgrades including primarily soil and not much rock or aggregate are excavated and the volume determined. In this example, the moisture content is not determined for each test site. Some regulatory agencies refer to this as the "short test" as it is a time saver that assumes the soil compacted in a mold has been brought to optimum moisture by the operator. The results are then related to the ratio of the volume of soil compacted in the mold Vm to the volume removed in-situ or percent compaction=Vm/Vs. Since Vm water is adjusted by the operator to be at optimum water content, it is then assumed to be at maximum density after packing in the mold. Hence a ratio of 1 means that the embankment or subgrade is at optimum density.

1) Prepare the test site by smoothing the surface;
2) Level and secure the optical template or frame on the test site;
3) Obtain a first or "flat" reading using the one or more material-interacting devices disclosed herein;
4) Dig a test hole, starting off with a spoon and continuing with an auger. Soil should be collected on a soil pan;
5) When hole is finished, remove the loose soil particles from the hole and contain it in a pan;
6) Obtain a second reading using the material-interacting device;
7) The volume of the hole can be determined by the difference between the second and first reading with the material-interacting device. If the volume is less than 910 cm^3, the hole is too small, and the user should remove additional material and repeat step 6;
8) If the hole is greater than 990 cm^3, the hole is too large, the user should move to a different location and start over;
9) Clean off excess soil from the auger and spoon and include in the soil pan;
10) Mix the soil until it has a uniform water content;
11) Check for optimum moisture using any experienced method such as the squeeze method;
12) Dry or add water as needed;
13) Move the soil to one side of the pan and divide into three equal layers;
14) Place first layer into a mold and apply compactive effort of 25 blows, checking to make sure the soil is compacting as expected assuming optimum moisture conditions;
15) Place the second layer in the mold including any rocks that were removed from the hole, and then apply compactive effort;
16) Place the $3^{rd}$ layer in the mold and apply compactive effort. After the $16^{th}$ blow, scrape any soil sticking to the ram rod and from the inside wall of the mold above the soil layer and apply the remaining blows;
17) Using the mold template for the material-interacting device, place the material-interacting device on the mold and obtain a reading of the volume of space above the soil in the mold;
18) The difference between the volume of the empty mold with a mold template and the soil filled material-interacting device mold-template volume is the volume of the soil occupying the mold; and
19) Determine the percent compaction by dividing the volume of soil compacted in the mold (step 18) by the volume of the hole (step 7) times 100.

Example 2

Sometimes the following test is referred to as the "long test" as it requires precise moisture measurements for each hole. In preparation, all loose soil in a 15 inch by 15 inch square is removed from the surface of the road and is brought to a smooth, flat, approximately level area by scraping with a steel straight edge or other suitable tool. A template for the material-interacting device is secured over the area and the material-interacting device is placed on the template and an initial pre-hole measurement of volume is obtained. The material-interacting device is removed and a hole is dug in the center of the template approximately 4 to 6 inches deep. The removed soil is placed in a container for weighing and determining moisture content by any gravimetric, thermal, suction, instrumented, electromagnetic, microwave, or chemical method. It is important that all of the soil removed is placed in the container as this is the mass related to the volume measurement. Once the hole is dug, the material-interacting device is placed again on the template and a new measurement of the void is obtained. The difference between the second material-interacting device and the first material-interacting device measurement is the volume of the hole. The volume of the hole should be no less than 780 cm^3.

The soil that is removed from the void is weighed and the moisture content is determined by any appropriate method. Non-nuclear methods are preferred, however, any approved method is acceptable. Once the dry weight of the soil is determined, and the volume of the void is known the dry density in-situ can be calculated.

Wet Density (mass/volume)=Wet weight/Volume

% $M$=(Wet wt.−Dry wt.)/Dry wt.×100

Dry Density=Wet Density/(100+Moisture content %)×100

1) Level the electronic scale;
2) Verify a 2 Kg weight is within 1 gram tolerance on the scale;
3) Weigh empty mold and record;
4) Prepare the test site by smoothing the surface;
5) Level and secure the template on the test site;
6) Obtain a first or "flat" reading using the optical hole reader (material-interacting device);
7) Dig a test hole, starting off with a spoon and continuing with an auger. Soil should be collected on a soil pan;
8) When hole is finished, remove the loose soil particles from the hole and include them in the pan;
9) Obtain a second reading using the material-interacting device;
10) The difference between the second and first reading with the material-interacting device is the volume of the hole. If the volume is less than 780 cm^3, the hole is too small, remove additional material and repeat step 6;
11) Clean off excess soil from the auger and spoon and include in the soil pan;
12) Place soil in drying pan, record weight of wet soil;
13) Mix soil until it has a uniform water content;
14) Dry the soil. When using a burner, be sure not to overheat the soil. When using a microwave oven, follow ASTM D 4643;
15) Weigh dry soil and record weight;
16) Record dry density in-situ from steps 15 and 10;
17) Remove additional soil from the hole and place in soil pan;
18) Break up and pulverize the soil;
19) Check for optimum moisture using the squeeze method;
20) Dry or add water to the soil as necessary, and mix for uniform water content. Repeat steps 18-19 until optimum moisture content is obtained;
21) Move the soil to one side of the pan and divide into three equal layers;
22) Place first later into a Proctor mold and apply compactive effort of 25 blows; check to make sure soil is compacting as expected assuming optimum moisture;
23) Place the second layer in the mold including any rocks that were removed from the hole, apply compactive effort;
24) Place the $3^{rd}$ layer in the mold and apply compactive effort. After the $16^{th}$ blow, scrape any soil sticking to the rammer and from the inside wall of the mold above the soil layer and apply the remaining blows;
25) Scribe around the top ($3^{rd}$) layer and then remove the mold collar;
26) The top of the $3^{rd}$ layer should be ¼ to ½ inch above the top of the mold;
27) Scrape off excess soil with the straight edge until the surface is flush with the top of the mold;
28) Weigh the mold with the soil and record the weight. Subtract out the weight of the mold;
29) Extract the soil pill from the mold;
30) Using the straight edge, split the soil pill down the middle lengthwise;
31) Obtain 300 g of soil by shaving the middle of the split pill from the top to bottom;
32) Dry the 300 g of soil, using a thermal method, find the water content; and
33) Obtain dry density with steps 32, 28 and the known volume of the mold.

Percent compaction=Dry Density of soil in-situ (step 16) divided by Dry Density of the soil compacted in mold (step 33)×100

Example 3

This test is used to calculate the degree of compaction of embankments and subgrades or soil bases that contain 33% aggregate, or have been stabilized by an admixture of aggregate material. This method uses a steel ring 18 inches OD and 4.5 to 9 inches deep.

The steel ring is placed over the area to be tested and the material within the ring is carefully loosened with a pick and removed with a scoop. The material removed is placed in the bucket for weighing. As the material is removed, the ring is lowered to the full depth of the layer by lightly tapping the top of the ring with a wooden mallet or similar object. After all the material has been removed, the ring is removed and the volume of the void is measured using optical methods.
1) Level the electronic scale;
2) Verify a 2 Kg weight is within 1 gram tolerance on the scale;
3) Tare a bucket;
4) Prepare the test site by smoothing the surface;
5) Level and secure the template on the test site;
6) Obtain a first or "flat" reading using the optical hole reader (material-interacting device);
7) Place the sampling ring on the surface to be tested within the area of the template;
8) Using a pick, loosen the material on the surface within the ring;
9) Remove the material and place in the bucket tapping the ring into the void as you go;
10) When hole is finished, remove the loose soil particles from the hole and include them in the bucket;
11) Weigh the material and record;
12) Remove the ring and obtain a second reading using the material-interacting device. (Alternatively, the measurement could be done with the ring in place). Volume can be calculated from the depth of the ring with it in place, or by the volume of the cylindrical ring with it removed;
13) The difference between the second and first reading with the material-interacting device is the volume of the void;
14) Find the density using 13 and 11;
15) Dump the material on the ground;
16) Quarter down the material and remix, do this twice. Purpose is to obtain a representative sample;
17) Place 1000 g of soil in drying pan, record weight of wet soil;
18) Dry the soil. When using a burner, be sure not to overheat the soil. When using a microwave oven, follow ASTM D 4643;
19) Weigh dry soil and record weight;
20) Record dry density in-situ from steps 19 and 13;
21) Obtain material from the quartered section and place in a soil pan until about ⅔ full;
22) Check for optimum moisture using the "squeeze" method;
23) Dry or add water to the soil as necessary, and mix for uniform water content. Repeat steps 22-23 until optimum moisture content is obtained;
24) Move the soil to one side of the pan and divide into three equal layers;
25) Place first layer into the large mold and apply compactive effort of 56 blows; check to make sure soil is compacting as expected assuming optimum moisture. (Note, a 3/40 ft^3 or 2123 cc mold should be used);
26) Place the second layer in the mold including any rocks that were removed from the hole, apply compactive effort;
27) Place the $3^{rd}$ layer in the mold and apply compactive effort. After the $35^{th}$ blow, scrape any soil sticking to the rammer and from the inside wall of the mold above the soil layer and apply the remaining blows;
28) Scribe around the top ($3^{rd}$) layer and then remove the mold collar;
29) The top of the $3^{rd}$ layer should be ¼ to ½ inch above the top of the mold;
30) Scrape off excess soil with the straight edge until the surface is flush with the top of the mold;
31) Weigh the mold with the soil and record the weight. Obtain the soil weight not including the mold;
32) Extract the soil pill from the mold;
33) Using the straight edge, split the soil pill down the middle lengthwise;
34) Obtain 1000 g of soil by shaving the middle of the split pill from the top to bottom;
35) Dry the soil, using a thermal method, find the water content;
36) Weigh the dry soil and record; and
37) Obtain dry density with steps 31, 35 and the known volume of the mold.

Percent compaction=Dry Density of soil in-situ (step 14) divided by Dry Density of the soil compacted in mold (step 36)×100

Example 4

The following test is used to calculate the degree of compaction of embankments and subgrades or having a high degree of compaction; otherwise known as Coarse aggregate base course. This method uses a steel ring having an outer diameter of 18 inches and 4.5 to 9 inches deep.

The steel ring is placed over the area to be tested and the base coarse material within the ring is carefully loosened with a pick and removed with a scoop. The material removed is placed in the bucket for weighing. As the material is removed, the ring is lowered to the full depth of the layer by lightly tapping the top of the ring with a wooden mallet or similar object. After all the material has been removed, the ring is removed and the volume of the void is measured using optical methods.

1) Level the electronic scale;
2) Verify a 2 Kg weight is within 1 gram tolerance on the scale;
3) Tare a bucket;
4) Prepare the test site by smoothing the surface;
5) Level and secure the template on the test site;
6) Obtain a first or "flat" reading using the optical hole reader (material-interacting device). (Note, other methods equivalent may not require a first reading);
7) Place the sampling ring on the surface to be tested within the area of the template;
8) Using a pick, loosen the material on the surface within the ring;
9) Remove the material and place in the bucket tapping the ring into the void as you go;
10) When hole is finished, remove the loose soil particles from the hole and include them in the bucket;
11) Weigh the material minus the bucket and record;
12) Remove the ring and obtain a second reading using the material-interacting device. (Alternatively, the measurement could be done with the ring in place). Volume can be calculated from the depth of the ring with it in place, or by the volume of the cylindrical ring with it removed;
13) The difference between the second and first reading with the material-interacting device is the volume of the void;
14) Find the wet density using 13 and 11;
15) Dump the material on the ground;
16) Quarter down the material and remix, do this twice. Purpose is to obtain a representative sample;
17) Place 1000 g of soil in drying pan, record weight of wet soil;
18) Dry the soil. When using a burner, be sure not to overheat the soil. When using a microwave oven, follow ASTM D 4643;
19) Weigh dry soil and record weight; and
20) Record dry density in-situ from steps 19 and 14.

Example 5

General Use

All of the above examples used some sort of Proctor mold for % Compaction comparisons. Note that in general, the density of a subbase could be determined simply by removing the soil with a tool, scanning and determining the volume of the hole, and weighing the soil and determining the density. Further determining the moisture content allows for the dry density of the soil to be found.

1) Level the electronic scale;
2) Verify a 2 Kg weight is within 1 gram tolerance on the scale;
3) Weigh empty mold and record;
4) Prepare the test site by smoothing the surface;
5) Level and secure the template on the test site;
6) Obtain a first or "flat" reading using the optical hole reader (material-interacting device);
7) Dig a test hole, starting off with a spoon and continuing with an auger. Soil should be collected on a soil pan;
8) When hole is finished, remove the loose soil particles from the hole and include them in the pan;

9) Obtain a second reading using the material-interacting device;
10) The difference between the second and first reading with the material-interacting device is the volume of the hole;
11) Clean off excess soil from the auger and spoon and include in the soil pan;
12) Place soil in drying pan, record weight of wet soil;
13) Mix soil until it has a uniform water content;
14) Dry the soil. When using a burner, be sure not to overheat the soil. When using a microwave oven, follow ASTM D 4643;
15) Weigh dry soil and record weight; and
16) Record dry density in-situ from steps 15 and 10.

In one or more embodiments, the material-interacting device 812 may also use confocal scanning In a confocal laser scanning microscope, a laser beam passes through a light source aperture and then is focused by an objective lens into a small (ideally diffraction limited) focal volume within or on the surface of a specimen. In biological applications especially, the specimen may be fluorescent. Scattered and reflected laser light as well as any fluorescent light from the illuminated spot is then re-collected by the objective lens. A beam splitter separates off some portion of the light into the detection apparatus, which in fluorescence confocal microscopy will also have a filter that selectively passes the fluorescent wavelengths while blocking the original excitation wavelength. After passing a pinhole, the light intensity is detected by a photodetection device (usually a photomultiplier tube (PMT) or avalanche photodiode), transforming the light signal into an electrical one that is recorded by a computer.

The detector aperture obstructs the light that is not coming from the focal point. The out-of-focus light is suppressed: most of the returning light is blocked by the pinhole, which results in sharper images than those from conventional fluorescence microscopy techniques and permits one to obtain images of planes at various depths within the sample (sets of such images are also known as z stacks).

The detected light originating from an illuminated volume element within the specimen represents one pixel in the resulting image. As the laser scans over the plane of interest, a whole image is obtained pixel-by-pixel and line-by-line, whereas the brightness of a resulting image pixel corresponds to the relative intensity of detected light. The beam is scanned across the sample in the horizontal plane by using one or more (servo controlled) oscillating mirrors. This scanning method usually has a low reaction latency and the scan speed can be varied. Slower scans provide a better signal-to-noise ratio, resulting in better contrast and higher resolution. Information can be collected from different focal planes by raising or lowering the microscope stage or objective lens. The computer can generate a three-dimensional picture of a specimen by assembling a stack of these two-dimensional images from successive focal planes.

Additionally, the material-interacting device 812 may be a range image device. The sensor device which is used for producing the range image is sometimes referred to as a range camera. Range cameras can operate according to a number of different techniques, some of which are presented here.

Stereo Triangulation

A stereo camera system can be used for determining the depth to points in the scene, for example, from the center point of the line between their focal points. In order to solve the depth measurement problem using a stereo camera system, it is necessary to first find corresponding points in the different images. Solving the correspondence problem is one of the main problems when using this type of technique. For instance, it is difficult to solve the correspondence problem for image points which lie inside regions of homogeneous intensity or color. As a consequence, range imaging based on stereo triangulation can usually produce reliable depth estimates only for a subset of all points visible in the multiple cameras. The correspondence problem is minimized in a plenoptic camera design, though depth resolution is limited by the size of the aperture, making it better suited for close-range applications.

The advantage of this technique is that the measurement is more or less passive; it does not require special conditions in terms of scene illumination. The other techniques mentioned here do not have to solve the correspondence problem but are instead dependent on particular scene illumination conditions.

Sheet of Light Triangulation

If the scene is illuminated with a sheet of light this creates a reflected line as seen from the light source. From any point out of the plane of the sheet, the line will typically appear as a curve, the exact shape of which depends both on the distance between the observer and the light source and the distance between the light source and the reflected points. By observing the reflected sheet of light using a camera (often a high resolution camera) and knowing the positions and orientations of both camera and light source, it is possible to determine the distances between the reflected points and the light source or camera.

By moving either the light source (and normally also the camera) or the scene in front of the camera, a sequence of depth profiles of the scene can be generated. These can be represented as a 2D range image.

Structured Light-3D Scanner

By illuminating the scene with a specially designed light pattern, structured light, depth can be determined using only a single image of the reflected light. The structured light can be in the form of horizontal and vertical lines, points, or checker board patterns.

Time-of-Flight

The depth can also be measured using the standard time-of-flight technique, more or less similar to radar or LIDAR, where a light pulse is used instead of an RF pulse. For example, a scanning laser, such as a rotating laser head, can be used to obtain a depth profile for points which lie in the scanning plane. This approach also produces a type of range image, similar to a radar image. Time-of-flight cameras are relatively new devices that capture a whole scene in three dimensions with a dedicated image sensor and therefore have no need for moving parts.

Interferometry

By illuminating points with coherent light and measuring the phase shift of the reflected light relative to the light source it is possible to determine depth, at least up to modulo the wavelength of the light. Under the assumption that the true range image is a more or less continuous function of the image coordinates, the correct depth can be obtained using a technique called phase-unwrapping.

By illuminating points with coherent light and measuring the phase shift of the reflected light relative to the light source it is possible to determine depth, at least up to modulo the wavelength of the light. Under the assumption that the true range image is a more or less continuous function of the image coordinates, the correct depth can be obtained using a technique called phase-unwrapping. In general, wavelength measurements are not useful for measurement on the order of the dimensions of an excavation. Wavelength dimensional methods are concerned with objects in the nearfield and cm type dimensions do not need that kind of accuracy or significant digits. However, if some kind of mineralogical composition or petrologic study was of interest, This might be implemented by focusing down a few centimeters, and then incorporating the interferometer techniques incorporating both farfield and nearfield objectives. For example, a characteristic might be 2.546 mm+0.5 lambda away from the reference.

Coded Aperture

Depth information may be partially or wholly inferred alongside intensity through reverse convolution of an image captured with a specially designed coded aperture pattern with a specific complex arrangement of holes through which the incoming light is either allowed through or blocked. The complex shape of the aperture creates a non-uniform blurring of the image for those parts of the scene not at the focal plane of the lens. Since the aperture design pattern is known, correct mathematical deconvolution taking account of this can identify where and by what degree the scene has become convoluted by out of focus light selectively falling on the capture surface, and reverse the process. Thus the blur-free scene may be retrieved and the extent of blurring across the scene is related to the displacement from the focal plane, which may be used to infer the depth. Since the depth for a point is inferred from its extent of blurring caused by the light spreading from the corresponding point in the scene arriving across the entire surface of the aperture and distorting according to this spread, this is a complex form of stereo triangulation. Each point in the image is effectively spatially sampled across the width of the aperture.

In accordance with one or more embodiments, a locating and tracking device may be employed within a system utilizing an apparatus, method, or system disclosed herein. Such a system is disclosed in US Patent Publication No. 20110066398, the entire contents of which are hereby incorporated by reference. Such a system may record information such as Project number, county, GPS location, data, test site name, first and second optical measurements, mold and mold collar volumes and serial numbers, weights, moisture contents, wet density, dry density, % compaction, Engineer, Inspector. A fully automated system could record results in a spread sheet.

The mass determining device could be in communication with a computer and the computer in communication with the optical system. Step by step procedures for the operator could be displayed on a display panel in one or more embodiments.

Various techniques described herein may be implemented with hardware or software or, where appropriate, with a combination of both. Thus, the methods and apparatus of the disclosed embodiments, or certain aspects or portions thereof, may take the form of program code (i.e., executable instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Therefore, it is to be understood that the subject matter disclosed herein is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An apparatus for optically interacting with a cylindrically-shaped construction material sample defining a longitudinal axis that extends from a central point of an end of the construction material sample, the apparatus comprising:
   a mechanism configured for rotating the construction material sample about the longitudinal axis;
   at least one material-interacting device spaced-apart from the mechanism and configured for an optical interaction with the construction material sample to generate multi-dimensional image data of an opaque surface of the construction material sample; and
   a computer device configured to generate one of surface data and bulk volumetric data of the construction material sample based on the multi-dimensional optical image data of the opaque surface of the construction material sample.

2. The apparatus of claim 1, wherein the mechanism comprises a translation mechanism having at least one roller wheel positioned about the construction material sample and configured to rotate or translate the construction material sample.

3. The apparatus of claim 1, wherein the at least one roller wheel is operably coupled to a motor configured to provide rotational forces thereto.

4. The apparatus of claim 1, further comprising a housing that carries the mechanism and the construction material sample.

5. The apparatus of claim 4, wherein the housing is configured to translate the construction material sample from a first position to at least a second position.

6. The apparatus of claim 1, wherein the at least one material-interacting device comprises a plurality of material-interacting devices spaced-apart from the mechanism.

7. The apparatus of claim 1, wherein the material-interacting device is configured to determine at least one measurement of the surface of the construction material sample.

8. The apparatus of claim 7, wherein the material-interacting device is configured to generate the at least one measurement to determine a characteristic of the construction material sample.

9. The apparatus of claim 8, wherein the characteristic is one of density, volume, and moisture content.

10. The apparatus of claim 1, wherein the at least one material-interacting device is configured to direct or to receive one of a light point, a light line, or a wave front on a surface of the construction material sample for interacting therewith.

11. The apparatus of claim 1, wherein the at least one material-interacting device is configured to direct or to receive one of sound, ultrasound, light, and radiation on the construction material sample for interacting therewith.

12. The apparatus of claim 1, wherein the at least one material-interacting device is configured to determine a characteristic of one or more surface voids defined in a surface of the construction material sample, and
wherein the computer device is configured to generate the volume data based on the characteristic of the one or more surface voids.

13. The apparatus of claim 1, wherein the at least one material-interacting device comprises at least one camera or lens positioned at different locations or angles and configured to capture stereo images of the construction material sample to generate the multi-dimensional image data.

14. The apparatus of claim 1, further comprising a light source configured to generate and to apply light to the construction material sample.

15. The apparatus of claim 1, further comprising:
one of an ambient, available, and natural light source that applies light to illuminate the construction material sample; and
an imaging device configured to generate multi-dimensional analysis of the construction material sample.

16. The apparatus of claim 1, wherein the at least one material-interacting device is configured to direct further including one of a light point, a light line, ambient light, coherent light, incoherent light, or a wave front directed on a surface of the construction material sample for interacting therewith including stereo vision techniques.

17. The apparatus of claim 1, wherein the at least one material-interacting device is configured to direct further including using one of sound, ultrasound, light, ambient light, available light, natural light, coherent light, and incoherent light directed on the construction material sample for interacting therewith.

18. The apparatus of claim 1, wherein the at least one material-interacting device comprises at least one camera or lens positioned at different locations or angles and configured to capture stereo images of the construction material sample to generate the multi-dimensional image data.

19. A method comprising:
rotating a cylindrically-shaped construction material sample along a longitudinal axis of the construction material sample;
interacting, using at least one material-interacting device, with the construction sample material by optical illumination interaction to generate multi-dimensional image data of an opaque surface of the construction material sample; and
generating, using a computer device, one of surface data and bulk volumetric data of the construction material sample based on the multi-dimensional optical image data of the opaque surface of the construction material sample.

20. The method of claim 19, wherein rotating the cylindrically-shaped construction material sample comprises using at least one roller wheel positioned about the construction material sample for rotating the construction material sample.

21. The method of claim 19, further including projecting one of a light point, a light line, or a wave front on a surface of the construction material sample for interacting therewith.

22. The method of claim 19, further including using one of sound, ultrasound and light for interacting with the construction material sample.

23. The method of claim 19, wherein the at least one material-interacting device further comprises at least one sample-imaging device, and
wherein the multi-dimensional image data defines one or more surface voids of the construction material sample.

24. The method of claim 23, further comprising using surface void data, surface irregularity or surface roughness to obtain an actual volume or a volume estimate of the construction material sample.

25. The method of claim 23, further comprising using volume data or surface void data and mass data of the construction material sample for calculating one of density and moisture content.

26. The method of claim 23, further comprising using the multi-dimensional image data defining the one or more surface voids to correct a dimensional volume or result.

27. The method of claim 19, wherein the surface data defines one of height, shape, texture, surface roughness, color, aggregate size, or combinations thereof of the construction material sample.

28. The method of claim 19, further comprising generating data of the construction material sample to create a histogram of the characteristics.

29. The method of claim 19, further comprising using a computer device for:
determining a characteristic of one or more surface voids defined in a surface of the construction material sample; and
generating the volume data based on the characteristic of the one or more surface voids.

30. The method of claim 19, wherein interacting with the construction material sample comprises using at least one camera or lens positioned at different locations or angles for capturing stereo images of the construction material sample to generate the multi-dimensional image data.

31. The method of claim 19, further comprising generating and applying light to the construction material sample.

32. The method of claim 19, further comprising:
applying one of an ambient, available, and natural light to the construction material sample; and
using an imaging device configured to generate multi-dimensional analysis of the construction material sample.

33. The method of claim 19, further including projecting one of a light point, a light line, ambient light, available light, natural light, coherent light, incoherent light, or a wave front on a surface of the construction material sample for interacting therewith including stereo vision techniques.

34. The method of claim 19, further including using one of sound, ultrasound, light, ambient light, available light, natural light, coherent light, and incoherent light for interacting with the construction material sample.

35. The method of claim 19, wherein interacting with the construction material sample comprises using at least one camera or lens positioned at different locations or angles for capturing stereo images of the construction material sample to generate the multi-dimensional image data.

* * * * *